(12) United States Patent
Gibson et al.

(10) Patent No.: US 9,849,237 B2
(45) Date of Patent: Dec. 26, 2017

(54) INJECTION SYSTEM WITH CAPACITIVE SENSING

(75) Inventors: Chad M. Gibson, Westerville, OH (US); Charles S. Neer, Cincinnati, OH (US)

(73) Assignee: LIEBEL-FLARSHEIM COMPANY LLC, Cincinnati, OH (US)

( * ) Notice: Subject to any disclaimer, the term of this patent is extended or adjusted under 35 U.S.C. 154(b) by 382 days.

(21) Appl. No.: 14/232,305

(22) PCT Filed: Jun. 26, 2012

(86) PCT No.: PCT/US2012/044163
§ 371 (c)(1),
(2), (4) Date: Jan. 13, 2014

(87) PCT Pub. No.: WO2013/012526
PCT Pub. Date: Jan. 24, 2013

(65) Prior Publication Data
US 2014/0142537 A1    May 22, 2014

Related U.S. Application Data

(60) Provisional application No. 61/508,734, filed on Jul. 18, 2011.

(51) Int. Cl.
*A61M 5/168* (2006.01)
*A61M 5/145* (2006.01)

(52) U.S. Cl.
CPC .... *A61M 5/16809* (2013.01); *A61M 5/14546* (2013.01); *A61M 5/16831* (2013.01);
(Continued)

(58) Field of Classification Search
CPC .......... A61M 25/0071; A61M 25/0021; A61M 25/0023; A61M 25/0032; A61M 39/0208
(Continued)

(56) References Cited

U.S. PATENT DOCUMENTS 4,006,736 A    2/1977 Kranys et al.
6,110,148 A  *  8/2000 Brown ................ A61M 5/1782
                                                222/23
(Continued)

FOREIGN PATENT DOCUMENTS

WO    2005077441 A2    8/2005
WO    2006/021295 A1   3/2006
(Continued)

*Primary Examiner* — Kevin C Sirmons
*Assistant Examiner* — Amber Stiles
(74) *Attorney, Agent, or Firm* — Marsh Fischmann & Breyfogle LLP

(57) ABSTRACT

A powerhead (50) of a power injector is disclosed that includes a syringe housing (110) that contains a capacitive fluid detector (112). The capacitive fluid detector (112) may be operable to detect fluid within a syringe (116) installed on the syringe housing (110). The output of the capacitive fluid detector (112) may be used to estimate the volume of fluid within the syringe (116). The capacitive fluid detector (112) may include a plurality of discrete capacitors (118*a*-118*h*) arranged serially along a longitudinal axis (120) of the syringe (116). Each of the plurality of capacitors (118*a*-118*h*) may be operable to produce an electric field extending into the syringe (116). Each of the plurality of capacitors (118*a*-118*h*) may be formed on a printed circuit board (130).

14 Claims, 14 Drawing Sheets

(52) U.S. Cl.
CPC .................. *A61M 5/14566* (2013.01); *A61M 2005/14553* (2013.01); *A61M 2205/3317* (2013.01); *A61M 2205/3389* (2013.01)

(58) Field of Classification Search
USPC .................. 604/288.01–288.04, 284, 111
See application file for complete search history.

(56) References Cited

U.S. PATENT DOCUMENTS

| | | | |
|---|---|---|---|
| 6,352,523 | B1 | 3/2002 | Brown et al. |
| 2001/0029315 | A1* | 10/2001 | Sakurai .......... A61B 17/320068 600/101 |
| 2007/0121230 | A1 | 5/2007 | Klein |
| 2007/0203460 | A1 | 8/2007 | Nemoto et al. |
| 2008/0033368 | A1* | 2/2008 | Fago .................. A61M 5/14546 604/189 |
| 2008/0177900 | A1 | 7/2008 | Grant et al. |
| 2009/0069756 | A1 | 3/2009 | Larsen |
| 2012/0019184 | A1 | 1/2012 | Niizuma |
| 2012/0136246 | A1 | 5/2012 | Martz |

FOREIGN PATENT DOCUMENTS

| | | |
|---|---|---|
| WO | 2006108026 A2 | 10/2006 |
| WO | 2007/107558 A2 | 9/2007 |
| WO | 2011/019776 A2 | 2/2011 |

* cited by examiner

INJECTION SYSTEM WITH CAPACITIVE SENSING

CROSS-REFERENCE TO RELATED APPLICATIONS

This patent application is a U.S. National Stage of PCT/US2012/044163, filed Jun. 26, 2012, which claims priority to and is a non-provisional application of U.S. Provisional Patent Application Ser. No. 61/508,734, entitled "INJECTION SYSTEM WITH CAPACITIVE SENSING," filed on Jul. 18, 2011. The entire disclosure of each patent application set forth in this Cross-Reference to Related Applications section is hereby incorporated by reference in their entirety herein. Priority is claimed to each patent application set forth in this Cross-Reference to Related Applications section.

FIELD OF THE INVENTION

The present invention generally relates to injection systems and, more particularly, to detecting fluid within a syringe used by the injection system.

BACKGROUND

Various medical procedures require that one or more medical fluids be injected into a patient. For example, medical imaging procedures oftentimes involve the injection of contrast media into a patient, possibly along with saline and/or other fluids. Other medical procedures involve injecting one or more fluids into a patient for therapeutic purposes. Power injectors may be used for these types of applications.

A power injector generally includes what is commonly referred to as a powerhead. One or more syringes may be mounted to the powerhead in various manners (e.g., detachably; rear-loading; front-loading; side-loading). Each syringe typically includes what may be characterized as a syringe plunger, piston, or the like. Each such syringe plunger is designed to interface with (e.g., contact and/or temporarily interconnect with) an appropriate syringe plunger driver that is incorporated into the powerhead, such that operation of the syringe plunger driver axially advances the associated syringe plunger inside and relative to a barrel of the syringe. One typical syringe plunger driver is in the form of a ram that is mounted on a threaded lead or drive screw. Rotation of the drive screw in one rotational direction advances the associated ram in one axial direction, while rotation of the drive screw in the opposite rotational direction advances the associated ram in the opposite axial direction.

SUMMARY

The first through fourth aspects of the present invention are each embodied by an injection system. The injection system includes an injection device and a syringe barrel zone. The injection system further comprises a capacitive fluid detector. The injection system is operable to hold a syringe such that a syringe barrel of the syringe is coextensive with the syringe barrel zone. The syringe barrel zone further includes a syringe barrel zone length coinciding with a syringe barrel length of a syringe when the syringe is held by the injection device. The syringe barrel zone further includes a syringe barrel zone longitudinal axis coinciding with a syringe barrel longitudinal axis of the syringe when the syringe is held by the injection device.

In the case of the first aspect, the capacitive fluid detector is disposed within the injection device. An electric field of the capacitive fluid detector penetrates the syringe barrel zone at least at a first position and a second position along the syringe barrel zone longitudinal axis. The first position is separated from the second position by a first distance that is equal to at least half of the syringe barrel zone length.

In the case of the second aspect, the capacitive fluid detector is disposed within the injection device, and an electric field of the capacitive fluid detector penetrates the syringe barrel zone at least at a first position and a second position along the syringe barrel zone longitudinal axis. The first position is separated from the second position by a first distance that is equal to at least half of the syringe barrel zone length. In the second aspect, the capacitive fluid detector includes a first capacitor. The first capacitor includes a first elongated electrode and a second elongated electrode. An electric field of the first capacitor penetrates the syringe barrel zone at least at the first position and the second position.

In the case of the third aspect, the capacitive fluid detector is disposed within the injection device. The capacitive fluid detector includes a first capacitor and a second capacitor. An electric field of the first capacitor penetrates the syringe barrel zone at a first position along the syringe barrel zone longitudinal axis. An electric field of the second capacitor penetrates the syringe barrel zone at the first position along the syringe barrel zone longitudinal axis.

In the case of the fourth aspect, the injection system includes a syringe mounted to the injection device. The syringe includes the syringe barrel. The syringe barrel has a syringe barrel length along the syringe barrel longitudinal axis. The capacitive fluid detector is disposed along the syringe barrel. The capacitive fluid detector includes a plurality of capacitors arranged serially along the syringe barrel length. Each of the plurality of capacitors is disposed at a different position along the syringe barrel longitudinal axis. The syringe barrel zone comprises a syringe barrel zone length coinciding with the syringe barrel length, and a syringe barrel zone longitudinal axis coinciding with the syringe barrel longitudinal axis A number of feature refinements and additional features are applicable to each of the above-noted first, second, third, and fourth aspects of the present invention. These feature refinements and additional features may be used individually or in any combination in relation to each of the first, second, third, and fourth aspects. As such, each of the following features that will be discussed may be, but are not required to be, used with any other feature or combination of features of each of the first, second, third, and fourth aspects. The following discussion is applicable to each of the first, second, third, and fourth aspects, up to the start of the discussion of the fifth aspect of the present invention.

As noted, the fourth aspect includes a plurality of capacitors arranged serially along the syringe barrel length (e.g., spaced along the syringe barrel length). Moreover, the first and third aspects may include a plurality of capacitors arranged serially along the syringe barrel zone length. In such arrangements that include a plurality of capacitors arranged serially along the syringe barrel zone length, the capacitive fluid detector may include at least eight capacitors arranged serially along the syringe barrel zone length. Each of the plurality of capacitors may include a pair of electrodes, and each electrode of each pair of electrodes may be arranged such that a vector perpendicular to and intersecting the electrode does not intersect any other electrode (e.g., the other electrode of the pair of electrodes and/or any electrode of any other capacitor of the plurality of capacitors). In an arrangement, each of the pair of electrodes of the plurality of capacitors may be substantially coplanar.

Each of the plurality of capacitors in arrangements that include a plurality of capacitors arranged serially along the syringe barrel zone length may be interconnected to a integrated circuit. For each of the plurality of capacitors, the integrated circuit may be operable to produce a bimodal output. A first mode of the bimodal output may be in response to a presence of fluid, and a second mode of the bimodal output may be in response to a lack of fluid. In this regard, the capacitors may be viewed as sensing the presence of fluid, sensing the absence of fluid (e.g., sensing air and/or vacuum), or both. In another arrangement, each of the plurality of capacitors may be operable to produce an analog output that varies in response to an amount of fluid within an electric field of the capacitor. The injection system may further include fluid level determination logic operable to determine a level of fluid within the syringe barrel zone at least partially based on outputs from the plurality of capacitors.

In an embodiment of the second aspect, the first and second elongated electrodes may be arranged such that a vector perpendicular to and intersecting the first elongated electrode does not intersect the second elongated electrode. The first elongated electrode may be substantially coplanar with the second elongated electrode. The first and second elongated electrodes may each be elongated in a direction parallel to the syringe barrel zone longitudinal axis. The first capacitor may be operable to produce an analog output in response to a presence of fluid within the syringe barrel zone. A volume of fluid within the syringe barrel zone may be inferred from the analog output. In an embodiment, the second aspect may further include fluid level determination logic operable to determine a level of fluid within the syringe barrel zone at least partially based on an output of the first capacitor.

In an embodiment of the first through fourth aspects, the injection system may further include user input determination logic operable to determine a user input at least partially based on output from the capacitive fluid detector. As such, the capacitive fluid detector may be operable to detect both a level of fluid within a syringe and a user input sensed by the capacitive fluid detector. Such a user input may be in the form of movement of a user's fingers along a syringe mounted to the injection device.

The injection system may further include a capacitive user input detector wherein an electric field of the capacitive user input detector penetrates a first region adjacent to the syringe barrel zone. When a user's finger is positioned within the first region, the electric field of the capacitive user input detector may be altered and, based on such alteration, input determination logic may be operable to determine a user input. In an arrangement, an electric field of the capacitive user input detector may penetrate a second region adjacent to the syringe barrel zone, and the second region may be on an opposite side of the syringe barrel zone than the first region. In such an arrangement, fingers placed within the first and second regions and on either side of the syringe barrel zone may be individually detected by the capacitive user input detector.

The fifth aspect is embodied by a method of operating an injection system. In this method, a syringe is installed onto an injection device and a ram of the injection device is then moved to produce a corresponding movement of a plunger of the syringe. The method includes contacting the plunger with the ram. The moving step is performed while the ram is in contact with the plunger. Also, during the moving step, fluid is capacitively sensed within a syringe barrel of the syringe at a plurality of times. At each of the plurality of times, a volume of fluid within the syringe is estimated. The estimating is at least partially based on the capacitively sensing steps.

A number of feature refinements and additional features are applicable to the above-noted fifth aspect of the present invention. These feature refinements and additional features may be used individually or in any combination in relation to the fifth aspect. As such, each of the following features that will be discussed may be, but are not required to be, used with any other feature or combination of features of the fifth aspect. The following discussion is applicable to the fifth aspect, up to the start of the discussion of the sixth aspect of the present invention.

The moving may include retracting and/or advancing the plunger. At each of the plurality of times, the ram may be disposed in a unique location. In a configuration, the capacitively sensing and estimating steps may be performed continuously during the moving step. The method may further include the steps of drawing fluid into the syringe during the moving step, and, for each one of the plurality of times, verifying that the estimated volume of fluid corresponds to a volume of the syringe between a nozzle of the syringe and the plunger. The method may also further include advancing the plunger to inject fluid into a patient.

The method may further include capacitively sensing a finger of a user proximate to the syringe barrel of the syringe and interpreting, by the injection system, the capacitive sensing as a user input to the injection system. In a variation, the method may include capacitively sensing two fingers of a user moving along opposite sides of the syringe barrel. Such capacitive sensing may be interpreted by the injection system as an input command to purge the syringe barrel.

The sixth aspect is embodied by a method of operating an injection system. In this method, a syringe is installed onto an injection device and then fluid is sensed within a syringe barrel of the syringe. The sensing is performed with first, second, and third capacitive sensors. While sensing, erroneous readings are identified based at least partly on comparing outputs from the first, second and third capacitive sensors acquired during the sensing step. In an embodiment of the sixth aspect, a total volume of fluid within the syringe may be estimated based on the sensing and identifying steps.

The seventh aspect is embodied by a method of operating an injection system. In this method, a syringe is installed onto an injection device, and the presence of fluid within the installed syringe is sensed with a first portion of a plurality of capacitive sensors.

A number of feature refinements and additional features are applicable to the above-noted seventh aspect of the present invention. These feature refinements and additional features may be used individually or in any combination in relation to the seventh aspect. As such, each of the following features that will be discussed may be, but are not required to be, used with any other feature or combination of features of the seventh aspect. The following discussion is applicable to the seventh aspect, up to the start of the discussion of the eighth aspect of the present invention.

The method may further include sensing an absence of fluid within the installed syringe with a second portion of the plurality of capacitive sensors, and estimating a total volume of fluid within the syringe based on at least one of the sensing steps (e.g., sensing the presence of fluid and/or sensing the absence of fluid). The estimating step may include calculating a percentage fill of the syringe based on the number of capacitive sensors in the first portion and/or the number of capacitive sensors in the second portion. In an arrangement, the estimating step may include looking up, in a look-up table, the total volume of fluid, in such an arrangement, the lookup table may contain values for the total volume of fluid corresponding to the number of capacitive sensors included in the first and/or second portions.

The syringe may contain the total volume of fluid during the installing step, and at least one of the sensing steps may be performed prior to injecting any fluid from the syringe into a patient. In this regard, the syringe may be a pre-filled syringe. Moreover, the method may further include inputting a value corresponding to the total volume of fluid into the injection system, and verifying that the estimated total volume of fluid corresponds to the inputted value. The inputting step may include manually entering the value corresponding to the total volume of fluid, scanning a machine readable label corresponding to the syringe, and/or reading a radio frequency identification (RFID) tag corresponding to the total volume of fluid.

The eighth aspect is embodied by a method of operating an injection system. In this method, a syringe is installed onto an injection device, and a user's finger is capacitively sensed proximate to the syringe. The capacitive sensing is then interpreted by the injection system as a user input to the injection system.

The ninth aspect is embodied by an injection system. The injection system includes an injection device and a syringe barrel zone. The injection system further includes a capacitive detector and user input determination logic. The injection system is operable to hold a syringe such that a syringe barrel of the syringe is coextensive with the syringe barrel zone. The syringe barrel zone further includes a syringe barrel zone length coinciding with a syringe barrel length of a syringe when the syringe is held by the injection device. The syringe barrel zone further includes a syringe barrel zone longitudinal axis coinciding with a syringe barrel longitudinal axis of the syringe when the syringe is held by the injection device. The injection device includes a capacitive detector. An electric field of the capacitive detector penetrates a first region adjacent to the syringe barrel zone. The user input determination logic is operable to determine a user input at least partially based on output from the capacitive detector.

A number of feature refinements and additional features are applicable to the above-noted ninth aspect of the present invention. These feature refinements and additional features may be used individually or in any combination in relation to the ninth aspect. As such, each of the following features that will be discussed may be, but are not required to be, used with any other feature or combination of features of the ninth aspect. The following discussion is applicable to the ninth aspect, up to the start of the discussion of the term "fluidly interconnected."

An electric field of the capacitive detector may penetrate a second region adjacent to the syringe barrel zone and on an opposite side of the syringe barrel zone from the first region. In such an arrangement, the user input determination logic may be operable to distinguish a user input within the first region from a user input within the second region, for example the user input determination logic may be operable to distinguish which side of the syringe barrel zone a user's finger is placed. The first and second regions may extend along substantially the entire syringe barrel zone length, and the user input determination logic may be operable to detect fingers of a user moving in the first and second regions along the syringe barrel zone length.

As used herein, the term "fluidly interconnected" refers to two or more components or entities being connected (directly or indirectly) in a manner such that fluid can flow (e.g., unidirectionally or bidirectionally) in a predetermined flow path therebetween. For example, "an injection device fluidly interconnected to a patient" describes a configuration where fluid can flow from the injection device through any interconnecting devices (e.g., tubing, connectors) and into the patient (e.g., into the vasculature of the patient).

As used herein, the term "detachably coupled" and the like describe a relationship between components where the components are interconnected yet retain the ability to be detached from each other where, after detaching, at least one of the components remains in a usable condition. For example, "the cassette and bulk fluid container holder module are detachably interconnected" describes a condition where the cassette is currently interconnected to the bulk fluid container holder module in a manner that allows for the cassette to be detached from the bulk fluid container holder module. Furthermore, after such detaching, at least one of the bulk fluid container holder module and the cassette retains the ability to be interconnected (e.g., detachably) with another component.

A number of feature refinements and additional features are separately applicable to each of above-noted first, second, third, fourth, fifth, sixth, seventh, eight, and ninth aspects of the present invention. These feature refinements and additional features may be used individually or in any combination in relation to each of the above-noted first, second, third, fourth, fifth, sixth, seventh, eighth and ninth aspects. Any feature of any other various aspects of the present invention that is intended to be limited to a "singular" context or the like will be clearly set forth herein by terms such as "only," "single," "limited to," or the like. Merely introducing a feature in accordance with commonly accepted antecedent basis practice does not limit the corresponding feature to the singular (e.g., indicating that a power injector includes "a syringe" alone does not mean that the power injector includes only a single syringe). Moreover, any failure to use phrases such as "at least one" also does not limit the corresponding feature to the singular (e.g., indicating that a power injector includes "a syringe" alone does not mean that the power injector includes only a single syringe). Finally, use of the phrase "at least generally" or the like in relation to a particular feature encompasses the corresponding characteristic and insubstantial variations thereof (e.g., indicating that a syringe barrel is at least generally cylindrical encompasses the syringe barrel being cylindrical).

Any "logic" that may be utilized by any of the various aspects of the present invention may be implemented in any appropriate manner, including without limitation in any appropriate software, firmware, or hardware, using one or more platforms, using one or more processors, using memory of any appropriate type, using any single computer of any appropriate type or a multiple computers of any appropriate type and interconnected in any appropriate manner, or any combination thereof. This logic may be implemented at any single location or at multiple locations that are interconnected in any appropriate manner (e.g., via any type of network).

Any power injector that may be utilized to provide a fluid discharge may be of any appropriate size, shape, configuration, and/or type. Any such power injector may utilize one or more syringe plunger drivers of any appropriate size, shape, configuration, and/or type, where each such syringe plunger driver is capable of at least bi-directional movement (e.g., a movement in a first direction for discharging fluid; a movement in a second direction for accommodating a loading and/or drawing of fluid and/or so as to return to a position for a subsequent fluid discharge operation), and where each such syringe plunger driver may interact with its corresponding syringe plunger in any appropriate manner (e.g., by mechanical contact; by an appropriate coupling (mechanical or otherwise)) so as to be able to advance the syringe plunger in at least one direction (e.g., to discharge fluid). Each syringe plunger driver may utilize one or more drive sources of any appropriate size, shape, configuration, and/or type. Multiple drive source outputs may be combined in any appropriate manner to advance a single syringe plunger at a given time. One or more drive sources may be dedicated to a single syringe plunger driver, one or more drive sources may be associated with multiple syringe plunger drivers (e.g., incorporating a transmission of sorts to change the output from one syringe plunger to another syringe plunger), or a combination thereof. Representative drive source forms include a brushed or brushless electric motor, a hydraulic motor, a pneumatic motor, a piezoelectric motor, or a stepper motor.

Any such power injector may be used for any appropriate application where the delivery of one or more medical fluids is desired, including without limitation any appropriate medical application (e.g., computed tomography or CT imaging; magnetic resonance imaging or MRI; single photon emission computed tomography or SPECT imaging; positron emission tomography or PET imaging; X-ray imaging; angiographic imaging; optical imaging; ultrasound imaging). Any such power injector may be used in conjunction with any component or combination of components, such as an appropriate imaging system (e.g., a CT scanner). For instance, information could be conveyed between any such power injector and one or more other components (e.g., scan delay information, injection start signal, injection rate).

Any appropriate number of syringes may be utilized with any such power injector in any appropriate manner (e.g., detachably; front-loaded; rear-loaded; side-loaded), any appropriate medical fluid may be discharged from a given syringe of any such power injector (e.g., contrast media, a radiopharmaceutical, saline, and any combination thereof), and any appropriate fluid may be discharged from a multiple syringe power injector configuration in any appropriate manner (e.g., sequentially, simultaneously), or any combination thereof. In one embodiment, fluid discharged from a syringe by operation of the power injector is directed into a conduit (e.g., medical tubing set), where this conduit is fluidly interconnected with the syringe in any appropriate manner and directs fluid to a desired location (e.g., to a catheter that is inserted into a patient for injection). Multiple syringes may discharge into a common conduit (e.g., for provision to a single injection site), or one syringe may discharge into one conduit (e.g., for provision to one injection site), while another syringe may discharge into a different conduit (e.g., for provision to a different injection site). In one embodiment, each syringe includes a syringe barrel and a plunger that is disposed within and movable relative to the syringe barrel. This plunger may interface with the power injector's syringe plunger drive assembly such that the syringe plunger drive assembly is able to advance the plunger in at least one direction, and possibly in two different, opposite directions.

DETAILED DESCRIPTION

Figure 1:
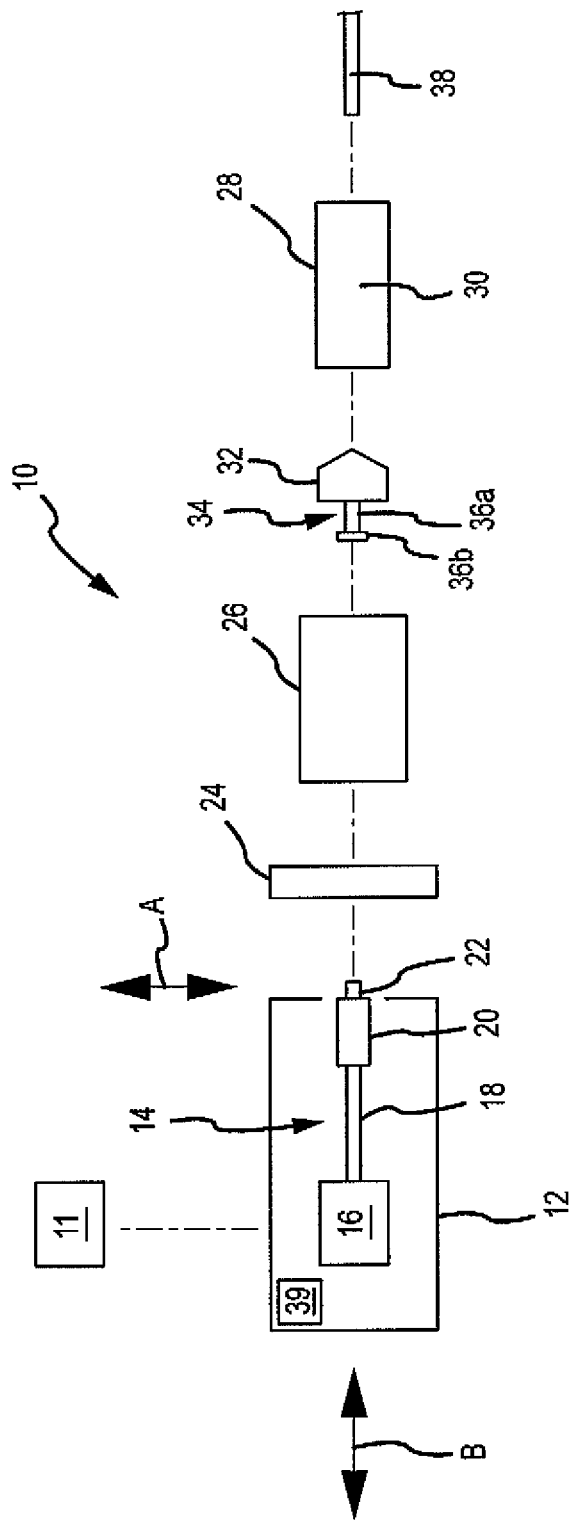
FIG. 1 is a schematic of one embodiment of a power injector.

FIG. 1 presents a schematic of one embodiment of a power injector 10 having a powerhead 12. One or more graphical user interfaces or GUIs 11 may be associated with the powerhead 12. Each GUI 11: 1) may be of any appropriate size, shape, configuration, and/or type; 2) may be operatively interconnected with the powerhead 12 in any appropriate manner; 3) may be disposed at any appropriate location; 4) may be configured to provide any of the following functions: controlling one or more aspects of the operation of the power injector 10; inputting/editing one or more parameters associated with the operation of the power injector 10; and displaying appropriate information (e.g., associated with the operation of the power injector 10); or 5) any combination of the foregoing. Any appropriate number of GUIs 11 may be utilized. In one embodiment, the power injector 10 includes a GUI 11 that is incorporated by a console that is separate from but which communicates with the powerhead 12. In another embodiment, the power injector 10 includes a GUI 11 that is part of the powerhead 12. In yet another embodiment, the power injector 10 utilizes one GUI 11 on a separate console that communicates with the powerhead 12, and also utilizes another GUI 11 that is on the powerhead 12. Each GUI 11 could provide the same functionality or set of functionalities, or the GUIs 11 may differ in at least some respect in relation to their respective functionalities.

A syringe 28 may be installed on the powerhead 12 and, when installed, may be considered to be part of the power injector 10. Some injection procedures may result in a relatively high pressure being generated within the syringe 28. In this regard, it may be desirable to dispose the syringe 28 within a pressure jacket 26. The pressure jacket 26 is typically associated with the powerhead 12 in a manner that allows the syringe 28 to be disposed therein as a part of or after installing the syringe 28 on the powerhead 12. The same pressure jacket 26 will typically remain associated with the powerhead 12, as various syringes 28 are positioned within and removed from the pressure jacket 26 for multiple injection procedures. The power injector 10 may eliminate the pressure jacket 26 if the power injector 10 is configured/ utilized for low-pressure injections and/or if the syringe(s) 28 to be utilized with the power injector 10 is (are) of sufficient durability to withstand high-pressure injections without the additional support provided by a pressure jacket 26. In any case, fluid discharged from the syringe 28 may be directed into a conduit 38 of any appropriate size, shape, configuration, and/or type, which may be fluidly interconnected with the syringe 28 in any appropriate manner, and which may direct fluid to any appropriate location (e.g., to a patient).

The powerhead 12 includes a syringe plunger drive assembly or syringe plunger driver 14 that interacts (e.g., interfaces) with the syringe 28 (e.g., a plunger 32 thereof) to discharge fluid from the syringe 28. This syringe plunger drive assembly 14 includes a drive source 16 (e.g., a motor of any appropriate size, shape, configuration, and/or type, optional gearing, and the like) that powers a drive output 18 (e.g., a rotatable drive screw). A ram 20 may be advanced along an appropriate path (e.g., axial) by the drive output 18. The ram 20 may include a coupler 22 for interacting or interfacing with a corresponding portion of the syringe 28 in a manner that will be discussed below.

The syringe 28 includes a plunger or piston 32 that is movably disposed within a syringe barrel 30 (e.g., for axial reciprocation along an axis coinciding with the double-headed arrow B). The plunger 32 may include a coupler 34. This syringe plunger coupler 34 may interact or interface with the ram coupler 22 to allow the syringe plunger drive assembly 14 to retract the syringe plunger 32 within the syringe barrel 30. The syringe plunger coupler 34 may be in the form of a shaft 36a that extends from a body of the syringe plunger 32, together with a head or button 36b. However, the syringe plunger coupler 34 may be of any appropriate size, shape, configuration, and/or type.

Generally, the syringe plunger drive assembly 14 of the power injector 10 may interact with the syringe plunger 32 of the syringe 28 in any appropriate manner (e.g., by mechanical contact; by an appropriate coupling (mechanical or otherwise)) so as to be able to move or advance the syringe plunger 32 (relative to the syringe barrel 30) in at least one direction (e.g., to discharge fluid from the corresponding syringe 28). That is, although the syringe plunger drive assembly 14 may be capable of bi-directional motion (e.g., via operation of the same drive source 16), the power injector 10 may be configured such that the operation of the syringe plunger drive assembly 14 actually only moves each syringe plunger 32 being used by the power injector 10 in only one direction. However, the syringe plunger drive assembly 14 may be configured to interact with each syringe plunger 32 being used by the power injector 10 so as to be able to move each such syringe plunger 32 in each of two different directions (e.g. in different directions along a common axial path).

Retraction of the syringe plunger 32 may be utilized to accommodate a loading of fluid into the syringe barrel 30 for a subsequent injection or discharge, may be utilized to actually draw fluid into the syringe barrel 30 for a subsequent injection or discharge, or for any other appropriate purpose. Certain configurations may not require that the syringe plunger drive assembly 14 be able to retract the syringe plunger 32, in which case the ram coupler 22 and syringe plunger coupler 34 may not be desired. In this case, the syringe plunger drive assembly 14 may be retracted for purposes of executing another fluid delivery operation (e.g., after another pre-filled syringe 28 has been installed). Even when a ram coupler 22 and syringe plunger coupler 34 are utilized, these components may or may not be coupled when the ram 20 advances the syringe plunger 32 to discharge fluid from the syringe 28 (e.g., the ram 20 may simply "push on" the syringe plunger coupler 34 or directly on a proximal end of the syringe plunger 32). Any single motion or combination of motions in any appropriate dimension or combination of dimensions may be utilized to dispose the ram coupler 22 and syringe plunger coupler 34 in a coupled state or condition, to dispose the ram coupler 22 and syringe plunger coupler 34 in an un-coupled state or condition, or both.

The syringe 28 may be installed on the powerhead 12 in any appropriate manner. For instance, the syringe 28 could be configured to be installed directly on the powerhead 12. In the illustrated embodiment, a housing 24 is appropriately mounted on the powerhead 12 to provide an interface between the syringe 28 and the powerhead 12. This housing 24 may be in the form of an adapter to which one or more configurations of syringes 28 may be installed, and where at least one configuration for a syringe 28 could be installed directly on the powerhead 12 without using any such adapter. The housing 24 may also be in the form of a faceplate to which one or more configurations of syringes 28 may be installed. In this case, it may be such that a faceplate is required to install a syringe 28 on the powerhead 12—the syringe 28 could not be installed on the powerhead 12 without the faceplate. When a pressure jacket 26 is being used, it may be installed on the powerhead 12 in the various manners discussed herein in relation to the syringe 28, and the syringe 28 will then thereafter be installed in the pressure jacket 26.

The housing 24 may be mounted on and remain in a fixed position relative to the powerhead 12 when installing a syringe 28. Another option is to movably interconnect the housing 24 and the powerhead 12 to accommodate installing a syringe 28. For instance, the housing 24 may move within a plane that contains the double-headed arrow A to provide one or more of coupled state or condition and an un-coupled state or condition between the ram coupler 22 and the syringe plunger coupler 34.

Figure 2A:
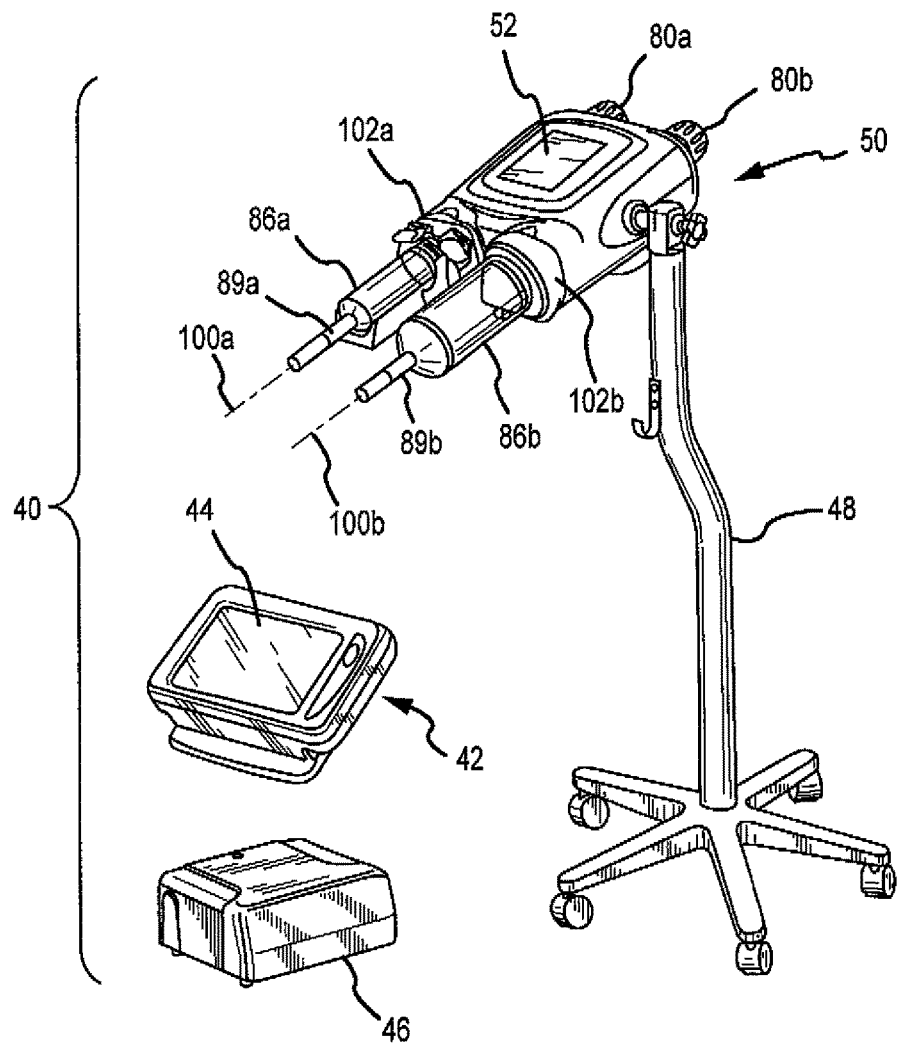
FIG. 2A is a perspective view of one embodiment of a portable stand-mounted, dual-head power injector.

One particular power injector configuration is illustrated in FIG. 2A, is identified by a reference numeral 40, and is at least generally in accordance with the power injector 10 of FIG. 1. The power injector 40 includes a powerhead 50 that is mounted on a portable stand 48. A pair of syringes 86a, 86b for the power injector 40 are mounted on the powerhead 50. Fluid may be discharged from the syringes 86a, 86b during operation of the power injector 40.

The portable stand 48 may be of any appropriate size, shape, configuration, and/or type. Wheels, rollers, casters, or the like may be utilized to make the stand 48 portable. The powerhead 50 could be maintained in a fixed position relative to the portable stand 48. However, it may be desirable to allow the position of the powerhead 50 to be adjustable relative to the portable stand 48 in at least some manner. For instance, it may be desirable to have the powerhead 50 in one position relative to the portable stand 48 when loading fluid into one or more of the syringes 86a, 86b, and to have the powerhead 50 in a different position relative to the portable stand 48 for performance of an injection procedure. In this regard, the powerhead 50 may be movably interconnected with the portable stand 48 in any appropriate manner (e.g., such that the powerhead 50 may be pivoted through at least a certain range of motion, and thereafter maintained in the desired position).

It should be appreciated that the powerhead 50 could be supported in any appropriate manner for providing fluid. For instance, instead of being mounted on a portable structure, the powerhead 50 could be interconnected with a support assembly, that in turn is mounted to an appropriate structure (e.g., ceiling, wall, floor). Any support assembly for the powerhead 50 may be positionally adjustable in at least some respect (e.g., by having one or more support sections that may be repositioned relative to one or more other support sections), or may be maintained in a fixed position. Moreover, the powerhead 50 may be integrated with any such support assembly so as to either be maintained in a fixed position or so as to be adjustable relative the support assembly.

The powerhead 50 includes a graphical user interface or GUI 52. This GUI 52 may be configured to provide one or any combination of the following functions: controlling one or more aspects of the operation of the power injector 40; inputting/editing one or more parameters associated with the operation of the power injector 40; and displaying appropriate information (e.g., associated with the operation of the power injector 40). The power injector 40 may also include a console 42 and powerpack 46 that each may be in communication with the powerhead 50 in any appropriate manner (e.g., via one or more cables), that may be placed on a table or mounted on an electronics rack in an examination room or at any other appropriate location, or both. The powerpack 46 may include one or more of the following and in any appropriate combination: a power supply for the injector 40; interface circuitry for providing communication between the console 42 and powerhead 50; circuitry for permitting connection of the power injector 40 to remote units such as remote consoles, remote hand or foot control switches, or other original equipment manufacturer (OEM) remote control connections (e.g., to allow for the operation of power injector 40 to be synchronized with the x-ray exposure of an imaging system); and any other appropriate componentry. The console 42 may include a touch screen display 44, which in turn may provide one or more of the following functions and in any appropriate combination: allowing an operator to remotely control one or more aspects of the operation of the power injector 40; allowing an operator to enter/edit one or more parameters associated with the operation of the power injector 40; allowing an operator to specify and store programs for automated operation of the power injector 40 (which can later be automatically executed by the power injector 40 upon initiation by the operator); and displaying any appropriate information relation to the power injector 40 and including any aspect of its operation.

Figure 2B:
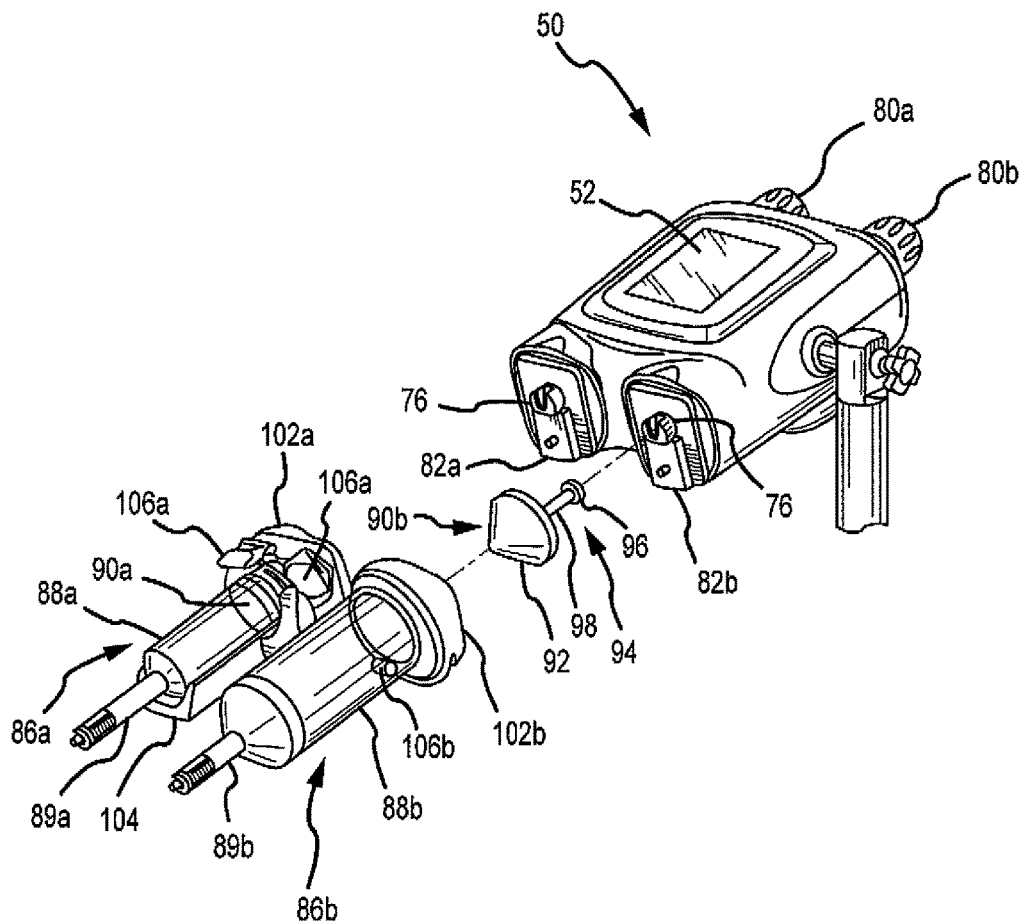
FIG. 2B is an enlarged, partially exploded, perspective view of a powerhead used by the power injector of FIG. 2A.

Various details regarding the integration of the syringes 86a, 86b with the powerhead 50 are presented in FIG. 2B. Each of the syringes 86a, 86b includes the same general components. The syringe 86a includes plunger or piston 90a that is movably disposed within a syringe barrel 88a. Movement of the plunger 90a along an axis 100a (FIG. 2A) via operation of the powerhead 50 will discharge fluid from within a syringe barrel 88a through a nozzle 89a of the syringe 86a. An appropriate conduit (not shown) will typically be fluidly interconnected with the nozzle 89a in any appropriate manner to direct fluid to a desired location (e.g., a patient). Similarly, the syringe 86b includes plunger or piston 90b that is movably disposed within a syringe barrel 88b. Movement of the plunger 90b along an axis 100b (FIG. 2A) via operation of the powerhead 50 will discharge fluid from within the syringe barrel 88b through a nozzle 89b of the syringe 86b. An appropriate conduit (not shown) will typically be fluidly interconnected with the nozzle 89b in any appropriate manner to direct fluid to a desired location (e.g., a patient).

The syringe 86a is interconnected with the powerhead 50 via an intermediate faceplate 102a. This faceplate 102a includes a cradle 104 that supports at least part of the syringe barrel 88a, and which may provide/accommodate any additional functionality or combination of functionalities. A mounting 82a is disposed on and is fixed relative to the powerhead 50 for interfacing with the faceplate 102a. A ram coupler 76 of a ram 74 (FIG. 2C), which are each part of a syringe plunger drive assembly or syringe plunger driver 56 (FIG. 2C) for the syringe 86a, is positioned in proximity to the faceplate 102a when mounted on the powerhead 50. Details regarding the syringe plunger drive assembly 56 will be discussed in more detail below in relation to FIG. 2C. Generally, the ram coupler 76 may be coupled with the syringe plunger 90a of the syringe 86a, and the ram coupler 76 and ram 74 (FIG. 2C) may then be moved relative to the powerhead 50 to move the syringe plunger 90a along the axis 100a (FIG. 2A). It may be such that the ram coupler 76 is engaged with, but not actually coupled to the syringe plunger 90a when moving the syringe plunger 90a to discharge fluid through the nozzle 89a of the syringe 86a.

The faceplate 102a may be moved at least generally within a plane that is orthogonal to the axes 100a, 100b (associated with movement of the syringe plungers 90a, 90b, respectively, and illustrated in FIG. 2A), both to mount the faceplate 102a on and remove the faceplate 102a from its mounting 82a on the powerhead 50. The faceplate 102a may be used to couple the syringe plunger 90a with its corresponding ram coupler 76 on the powerhead 50. In this regard, the faceplate 102a includes a pair of handles 106a. Generally and with the syringe 86a being initially positioned within the faceplate 102a, the handles 106a may be moved to in turn move/translate the syringe 86a at least generally within a plane that is orthogonal to the axes 100a, 100b (associated with movement of the syringe plungers 90a, 90b, respectively, and illustrated in FIG. 2A). Moving the handles 106a to one position moves/translates the syringe 86a (relative to the faceplate 102a) in an at least generally downward direction to couple its syringe plunger 90a with its corresponding ram coupler 76. Moving the handles 106a to another position moves/translates the syringe 86a (relative to the faceplate 102a) in an at least generally upward direction to uncouple its syringe plunger 90a from its corresponding ram coupler 76.

The syringe 86b is interconnected with the powerhead 50 via an intermediate faceplate 102b. A mounting 82b is disposed on and is fixed relative to the powerhead 50 for interfacing with the faceplate 102b. A ram coupler 76 of a ram 74 (FIG. 2C), which are each part of a syringe plunger drive assembly 56 for the syringe 86b, is positioned in proximity to the faceplate 102b when mounted to the powerhead 50. Details regarding the syringe plunger drive assembly 56 again will be discussed in more detail below in relation to FIG. 2C. Generally, the ram coupler 76 may be coupled with the syringe plunger 90b of the syringe 86b, and the ram coupler 76 and ram 74 (FIG. 2O) may be moved relative to the powerhead 50 to move the syringe plunger 90b along the axis 100b (FIG. 2A). It may be such that the ram coupler 76 is engaged with, but not actually coupled to, the syringe plunger 90*b* when moving the syringe plunger 90*b* to discharge fluid through the nozzle 89*b* of the syringe 86*b*.

The faceplate 102*b* may be moved at least generally within a plane that is orthogonal to the axes 100*a*, 100*b* (associated with movement of the syringe plungers 90*a*, 90*b*, respectively, and illustrated in FIG. 2A), both to mount the faceplate 102*b* on and remove the faceplate 102*b* from its mounting 82*b* on the powerhead 50. The faceplate 102*b* also may be used to couple the syringe plunger 90*b* with its corresponding ram coupler 76 on the powerhead 50. In this regard, the faceplate 102*b* may include a handle 106*b*. Generally and with the syringe 86*b* being initially positioned within the faceplate 102*b*, the syringe 86*b* may be rotated along its long axis 100*b* (FIG. 2A) and relative to the faceplate 102*b*. This rotation may be realized by moving the handle 106*b*, by grasping and turning the syringe 86*b*, or both. In any case, this rotation moves/translates both the syringe 86*b* and the faceplate 102*b* at least generally within a plane that is orthogonal to the axes 100*a*, 100*b* (associated with movement of the syringe plungers 90*a*, 90*b*, respectively, and illustrated in FIG. 2A). Rotating the syringe 86*b* in one direction moves/translates the syringe 86*b* and faceplate 102*b* in an at least generally downward direction to couple the syringe plunger 90*b* with its corresponding ram coupler 76. Rotating the syringe 86*b* in the opposite direction moves/translates the syringe 86*b* and faceplate 102*b* in an at least generally upward direction to uncouple its syringe plunger 90*b* from its corresponding ram coupler 76.

As illustrated in FIG. 2B, the syringe plunger 90*b* includes a plunger body 92 and a syringe plunger coupler 94. This syringe plunger coupler 94 includes a shaft 98 that extends from the plunger body 92, along with a head 96 that is spaced from the plunger body 92. Each of the ram couplers 76 includes a larger slot that is positioned behind a smaller slot on the face of the ram coupler 76. The head 96 of the syringe plunger coupler 94 may be positioned within the larger slot of the ram coupler 76, and the shaft 98 of the syringe plunger coupler 94 may extend through the smaller slot on the face of the ram coupler 76 when the syringe plunger 90*b* and its corresponding ram coupler 76 are in a coupled state or condition. The syringe plunger 90*a* may include a similar syringe plunger coupler 94 for interfacing with its corresponding ram coupler 76.

Figure 2C:
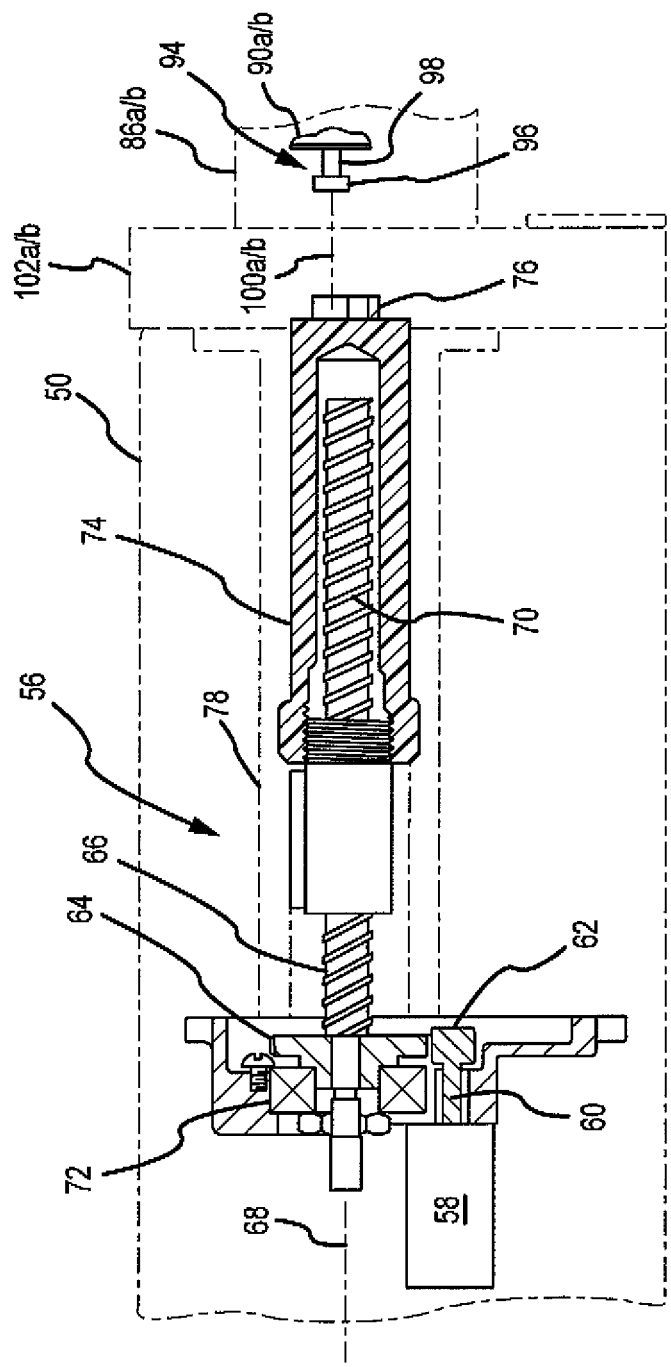
FIG. 2C is a schematic of one embodiment of a syringe plunger drive assembly used by the power injector of FIG. 2A.

The powerhead 50 is utilized to discharge fluid from the syringes 86*a*, 86*b* in the case of the power injector 40. That is, the powerhead 50 provides the motive force to discharge fluid from each of the syringes 86*a*, 86*b*. One embodiment of what may be characterized as a syringe plunger drive assembly or syringe plunger driver is illustrated in FIG. 2C, is identified by reference numeral 56, and may be utilized by the powerhead 50 to discharge fluid from each of the syringes 86*a*, 86*b*. A separate syringe plunger drive assembly 56 may be incorporated into the powerhead 50 for each of the syringes 86*a*, 86*b*. In this regard and referring back to FIGS. 2A-B, the powerhead 50 may include hand-operated knobs 80*a* and 80*b* for use in separately controlling each of the syringe plunger drive assemblies 56.

Initially and in relation to the syringe plunger drive assembly 56 of FIG. 2C, each of its individual components may be of any appropriate size, shape, configuration and/or type. The syringe plunger drive assembly 56 includes a motor 58, which has an output shaft 60. A drive gear 62 is mounted on and rotates with the output shaft 60 of the motor 58. The drive gear 62 is engaged or is at least engageable with a driven gear 64. This driven gear 64 is mounted on and rotates with a drive screw or shaft 66. The axis about which the drive screw 66 rotates is identified by reference numeral 68. One or more bearings 72 appropriately support the drive screw 66.

A carriage or ram 74 is movably mounted on the drive screw 66. Generally, rotation of the drive screw 66 in one direction axially advances the ram 74 along the drive screw 66 (and thereby along axis 68) in the direction of the corresponding syringe 86*a/b*, while rotation of the drive screw 66 in the opposite direction axially advances the ram 74 along the drive screw 66 (and thereby along axis 68) away from the corresponding syringe 86*a/b*. In this regard, the perimeter of at least part of the drive screw 66 includes helical threads 70 that interface with at least part of the ram 74. The ram 74 is also movably mounted within an appropriate bushing 78 that does not allow the ram 74 to rotate during a rotation of the drive screw 66. Therefore, the rotation of the drive screw 66 provides for an axial movement of the ram 74 in a direction determined by the rotational direction of the drive screw 66.

The ram 74 includes a coupler 76 that that may be detachably coupled with a syringe plunger coupler 94 of the syringe plunger 90*a/b* of the corresponding syringe 86*a/b*. When the ram coupler 76 and syringe plunger coupler 94 are appropriately coupled, the syringe plunger 90*a/b* moves along with ram 74. FIG. 2C illustrates a configuration where the syringe 86*a/b* may be moved along its corresponding axis 100*a/b* without being coupled to the ram 74. When the syringe 86*a/b* is moved along its corresponding axis 100*a/b* such that the head 96 of its syringe plunger 90*a/b* is aligned with the ram coupler 76, but with the axes 68 still in the offset configuration of FIG. 2C, the syringe 86*a/b* may be translated within a plane that is orthogonal to the axis 68 along which the ram 74 moves. This establishes a coupled engagement between the ram coupler 76 and the syringe plunger coupler 96 in the above-noted manner.

The power injectors 10, 40 of FIGS. 1 and 2A-C each may be used for any appropriate application, including without limitation for medical imaging applications where fluid is injected into a subject (e.g., a patient). Representative medical imaging applications for the power injectors 10, 40 include without limitation computed tomography or CT imaging, magnetic resonance imaging or MRI, single photon emission computed tomography or SPECT imaging, positron emission tomography or PET imaging, X-ray imaging, angiographic imaging, optical imaging, and ultrasound imaging. The power injectors 10, 40 each could be used alone or in combination with one or more other components. The power injectors 10, 40 each may be operatively interconnected with one or more components, for instance so that information may be conveyed between the power injector 10, 40 and one or more other components (e.g., scan delay information, injection start signal, injection rate).

Any number of syringes may be utilized by each of the power injectors 10, 40, including without limitation single-head configurations (for a single syringe) and dual-head configurations (for two syringes). In the case of a multiple syringe configuration, each power injector 10, 40 may discharge fluid from the various syringes in any appropriate manner and according to any timing sequence (e.g., sequential discharges from two or more syringes, simultaneous discharges from two or more syringes, or any combination thereof). Multiple syringes may discharge into a common conduit (e.g., for provision to a single injection site), or one syringe may discharge into one conduit (e.g., for provision to one injection site), while another syringe may discharge into a different conduit (e.g., for provision to a different injection site). Each such syringe utilized by each of the power injectors 10, 40 may include any appropriate fluid (e.g., a medical fluid), for instance contrast media, a radiopharmaceutical, saline, and any combination thereof. Each such syringe utilized by each of the power injectors 10, 40 may be installed in any appropriate manner (e.g., rear-loading configurations may be utilized; front-loading configurations may be utilized; side-loading configurations may be utilized).

Figure 3A:
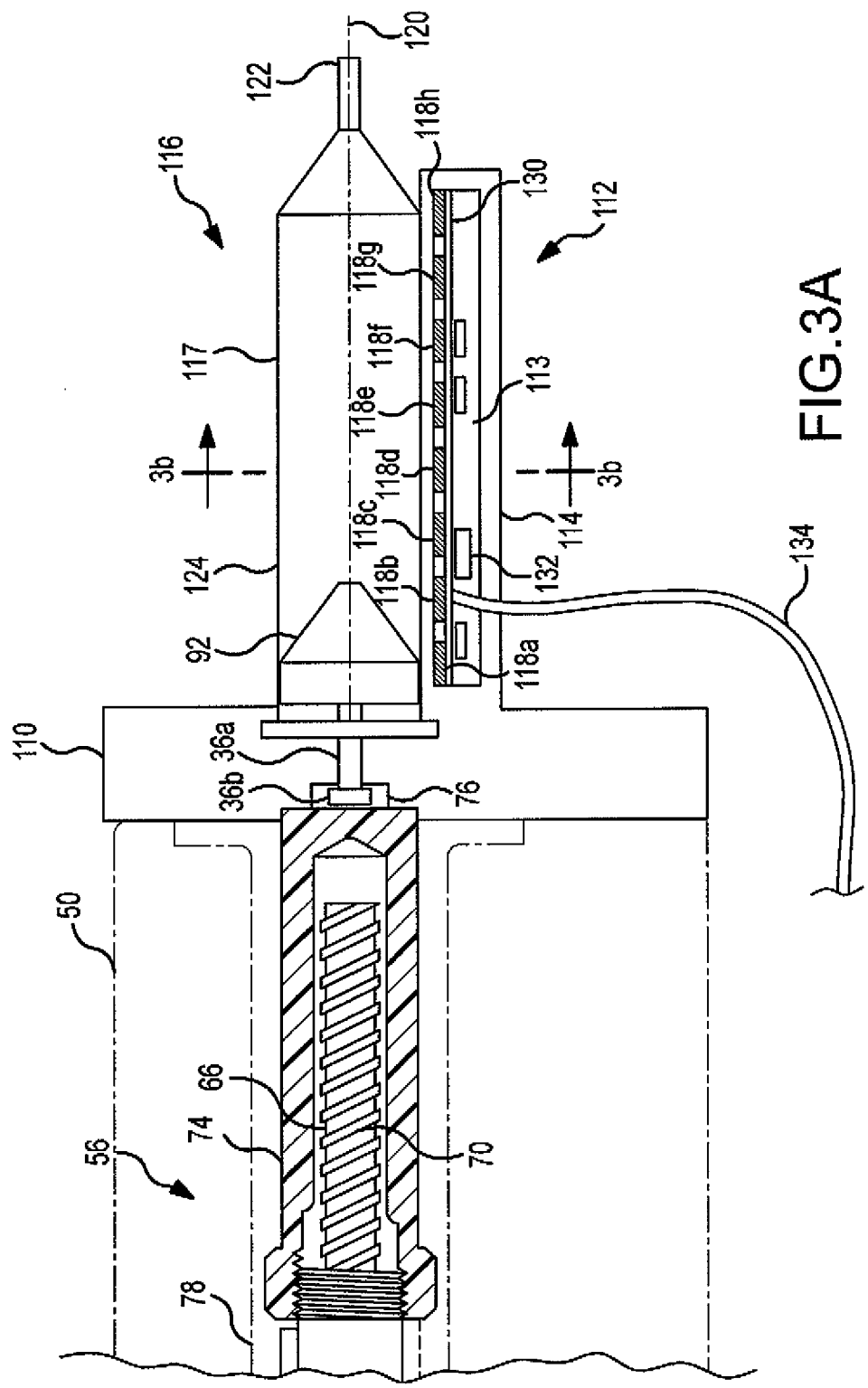
FIG. 3A is a schematic of a syringe housing that incorporates a capacitive fluid detector.

FIG. 3A is a schematic of a syringe housing 110 interconnected to the powerhead 50 of FIG. 2C. The syringe housing 110 includes a capacitive fluid detector 112. The syringe housing 110 may include a syringe support portion or cradle 114, which may be operable to support and/or be positioned along a syringe 116. In the illustrated embodiment, the capacitive fluid detector 112 is disposed within an interior 113 of the syringe support portion 114 (e.g., the capacitive fluid detector 112 may be encased or enclosed within the syringe housing 110).

The syringe housing 110 may be of any appropriate size, shape, configuration, and/or type. In the illustrated embodiment, the syringe housing 110 is appropriately mounted on or otherwise integrated with the powerhead 50 to provide an interface between the syringe 116 and the powerhead 50. The syringe housing 110 may be permanently attached to or incorporated by the powerhead 50, or at least installed thereon with proper tooling. The syringe housing 110 may also be in the form of an adapter to allow different configurations of syringes 116 to be installed on the powerhead 50 (e.g., an adapter may be installed on a syringe interface structure on the powerhead so a different syringe may be used—one syringe may be used with the syringe interface structure of the powerhead, and another syringe may be used when an appropriate adapter is installed on the powerhead). The syringe housing 110 may also be in the form of a faceplate to which one or more configurations of syringes 116 may be installed, and which may be installed on the powerhead 50 without any tooling (e.g., simply by hand). In this case, it may be such that a faceplate is required to install any syringe 116 on the powerhead 50—the syringe 116 could not be installed on the powerhead 50 without the faceplate in this instance.

The capacitive fluid detector 112 generally includes a printed circuit board (PCB) 130, individual capacitors 118a through 118h, and sensor electronics 132. The capacitors 118a-118h may be disposed on the PCB 130. The individual plates of each capacitor 118a-118h may be formed from a conductive layer or layers of the PCB 130 using well-known PCB manufacturing processes (e.g., etching, photolithography). Alternatively, the plates of the capacitors 118a-118h may be discrete components that are interconnected (e.g., separately mounted) to the PCB 130. The sensor electronics 132 also may be mounted on the PCB 130. The sensor electronics 132 may include components operable to output a signal to the capacitors 118a-118h to generate their respective electric fields and/or components operable to determine the capacitance of each individual capacitor 118a-118h. The sensor electronics 132 may, for example, include an integrated circuit capable of detecting capacitance changes to interconnected capacitors 118a-118h. One such integrated circuit is a QT1080 8 Key QTouch™ Sensor IC produced by Quantum Research Group, Pittsburgh, Pa.

The PCB 130 and devices interconnected thereto may be mounted to, and sealed, within the interior 113 of the syringe housing 110. In this regard, the PCB 130 may be protected from potential fluid spills and/or damage from direct contact. The syringe housing 110 may be communicatively interconnected to the powerhead 50 and/or other components of the power injector 40 via a cable 134. Other methods of communicatively interconnecting the syringe housing 110 to the powerhead 50 and/or other components of the power injector 40 may be utilized in conjunction with, or in place of, the cable 134. For instance, the syringe housing 110 may wirelessly communicate with the power injector 40. In another example, the syringe housing 110 may include conductive members that conductively mate with corresponding members on the powerhead 50 when the syringe housing 110 is installed on the powerhead 50.

The capacitive fluid detector 112 may generally be used to determine, infer, and/or estimate a volume of fluid disposed within a syringe barrel zone 124 (discussed below). In this regard, the volume of fluid within a pre-filled syringe upon installation may be determined by the capacitive fluid detector 112. Furthermore, the volume of fluid within a syringe may be determined by the capacitive fluid detector 112 at any appropriate time while the syringe is mounted to the syringe housing 110 (e.g., prior to and/or during an injection procedure). As used herein, "fluid" refers to non-gas fluids including fluids that may have a relatively high viscosity but are suitable for injection into a patient and including materials that may have multiple constituents, such as suspensions and colloids (e.g., emulsions).

The capacitive fluid detector 112 includes eight individual capacitors 118a through 118h arranged parallel to and spaced along a longitudinal axis 120 of the syringe 116 installed on the syringe housing 110. Any appropriate number of capacitors may be utilized. Additional capacitors may be positioned along tubing (not shown) attached to a nozzle 122 of the syringe 116. The capacitors 118a-118h may be arranged such that each individual capacitor 118a-118h may detect fluid in a predetermined portion of the syringe barrel zone 124. The syringe barrel zone 124 is defined as the maximum volume of space positioned relative to the syringe housing 110 that may be occupied by a barrel (e.g., a barrel 117 of syringe 116) of any appropriate syringe when that syringe is mounted to the syringe housing 110. The syringe barrel zone 124 may include a syringe barrel zone length coinciding with the length of the syringe barrel 117 when the syringe 116 is installed on the syringe housing 110. The syringe barrel zone 124 may include a syringe barrel zone longitudinal axis coinciding with the syringe barrel longitudinal axis 120 when the syringe 116 is installed on the syringe housing. As shown in FIG. 3A, the first capacitor 118a of the capacitive fluid detector 112 may be positioned to detect fluid within the syringe barrel zone 124 at or near where the plunger body 92 is located when the plunger body 92 is in a fully retracted position within syringe barrel 117 (as shown in FIG. 3A). Moreover, the last capacitor 118h may be positioned to detect fluid at or near the nozzle 122 end of the syringe 116. The remaining capacitors 118b through 118g may, for example, be equidistantly spaced between the first and last capacitors 118a, 118h. In this regard, the capacitors may be spaced along the entire length of the syringe barrel zone 124. Although discussed herein in terms of detecting fluid (e.g., capacitance below a certain level may indicate fluid is present), the capacitors described herein may also be viewed as detecting air, vacuum, or the lack of fluid (e.g., capacitance above a certain level may indicate air is present).

Figure 3B:
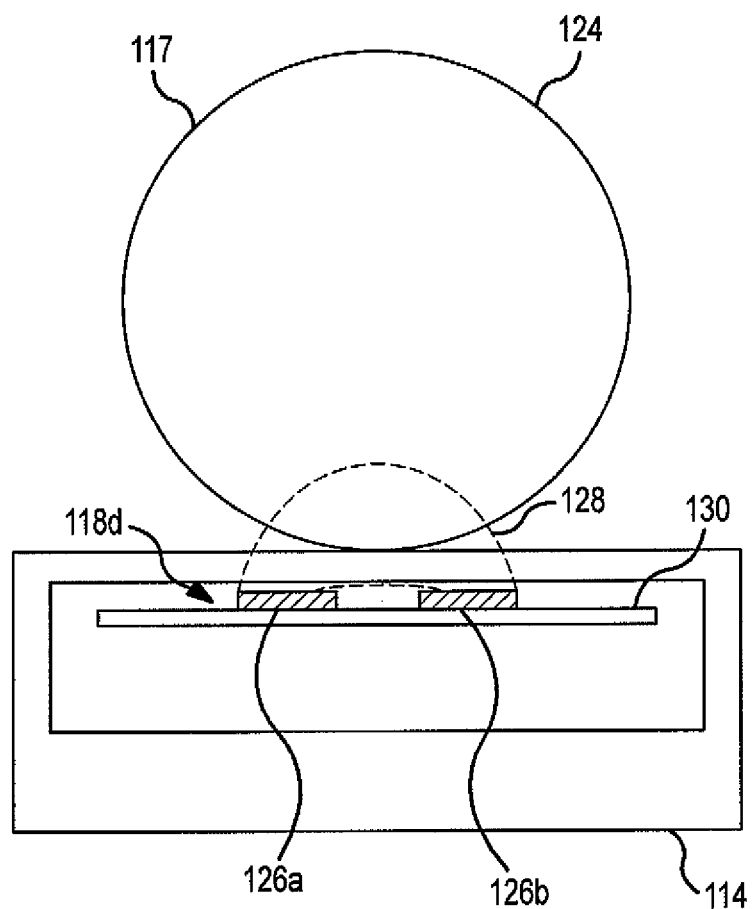
FIG. 3B is a cross-sectional schematic (end view) of the syringe housing and syringe of FIG. 3A.
Figure 3C:
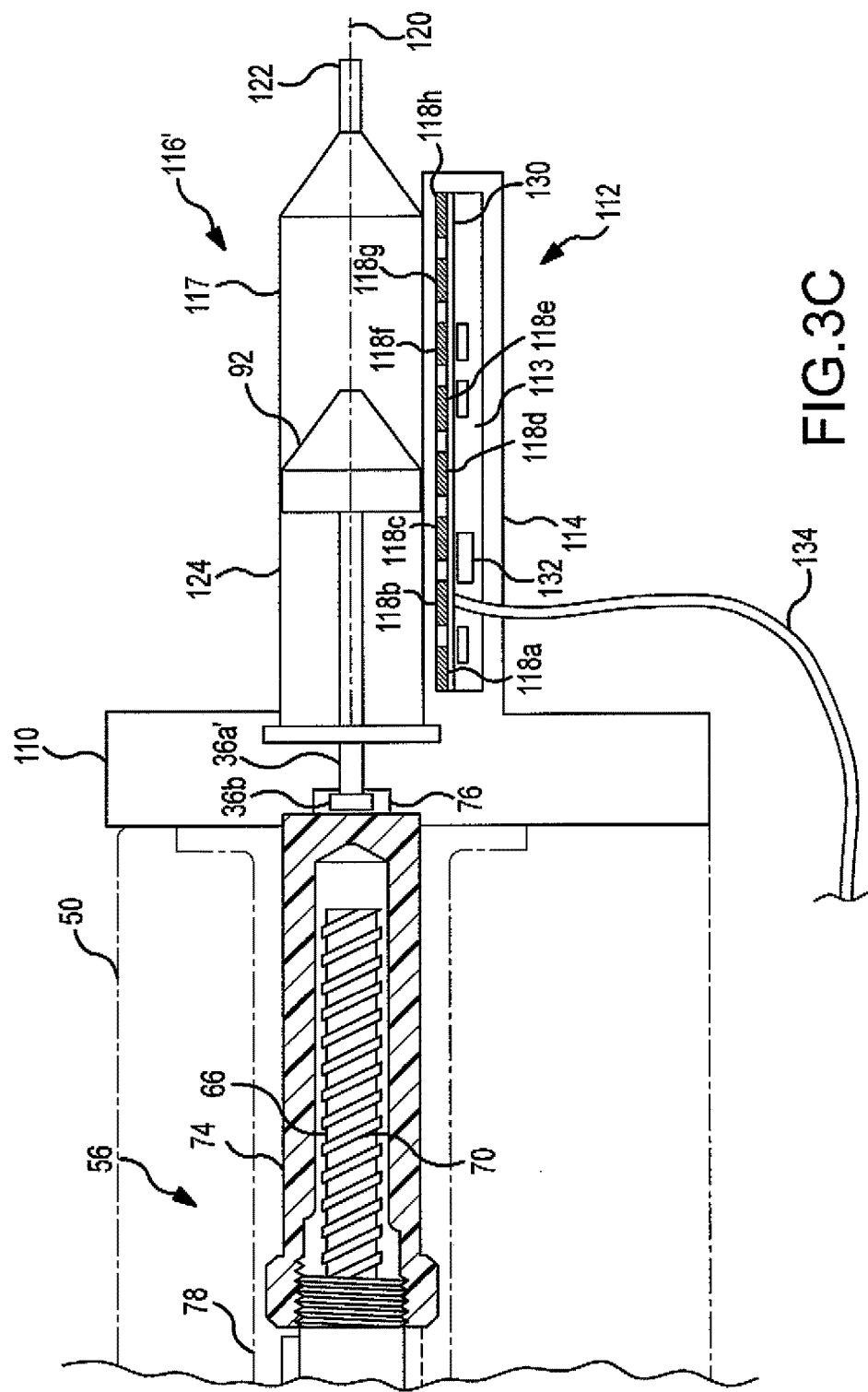
FIG. 3C is a schematic (side view) of the syringe housing and capacitive fluid detector of FIG. 3A with a different syringe installed thereon.

In some instances, such as illustrated in FIG. 3C, a syringe 116' may be installed onto the syringe housing 110 where the syringe 116' contains a volume of fluid that is smaller than the syringe barrel zone 124. Accordingly, the syringe 116' may have its plunger body 92 initially positioned as shown in FIG. 3C (the plunger 92 of syringe 116' may be shown in its fully retracted state) such that the volume within the syringe 116' between the plunger body 92 and the nozzle 122 is substantially equal to the volume of fluid contained therein (e.g., there is no air within the volume between the plunger body 92 and the nozzle 122). Consequently, the syringe 116' may have a corresponding shaft 36a' whose length is selected to position the button 36b in the same initial position as with a syringe 116. In this regard, the process of initially installing the syringe 116' onto the syringe housing 110, including interconnecting the button 36b to the ram coupler 76, may be similar to the process of initially installing the syringe 116 onto the syringe housing 110. In a similar manner, other syringes containing differing initial fluid volumes and corresponding differing shafts may be installed onto the syringe housing 110.

In alternate arrangements, the capacitive fluid detector 112 may contain any appropriate number of capacitors. Such capacitors may be placed in any appropriate pattern along the syringe barrel zone 124. For example, such capacitors may be equally spaced or they may be placed in a non-uniform manner. Capacitors may be spaced in a non-uniform manner to enable the capacitive fluid detector 112 to distinguish between installed syringes that initially contain different volumes of fluid. The capacitors may be disposed along a portion of the syringe barrel zone 124 that is less than the entire length of the syringe barrel zone 124.

Each of the capacitors 118a-118h of the capacitive fluid detector 112 may be in the form of two plates arranged side by side. The plates of each individual capacitor 118a-118h may be substantially coplanar. FIG. 3B is a cross-sectional schematic view of the syringe barrel zone 124 and syringe housing 110 of FIG. 3A along line 3b. The cross section cuts through capacitor 118d. Capacitor 118d may include two substantially coplanar plates 126a, 126b arranged side by side, and when the capacitor 118d is energized, an electric field 128 may be formed in a generally arc-shaped volume 128 extending upward and between the plates 126a, 126b. A portion of the electric field 128 may coincide with a portion of the syringe barrel zone 124.

The size and shape of the electric field 128 depicted in FIG. 3B is for exemplary purposes. The actual size and shape of the electric field 128 generated by the capacitor 118d may be dependent on several factors including, but not limited to, the size and shape of the capacitor plates 126a, 126b, the positioning of the capacitor plates 126a, 126b relative to each other, and the voltage level of the plates 126a, 126b. Furthermore, the sensitivity of the sensor electronics 132 may affect the usable size of the electric field 128. For example, sensor electronics 132 with a greater capacitance sensitivity may be able to detect capacitance changes due to objects at the fringe of the electric field 128, while sensor electronics 132 with a lower sensitivity may not be able to detect such capacitance changes. Accordingly, the size and shape of the electric field 128 may vary considerably from that depicted in FIG. 3B. For instance, in an arrangement, the electric field 128 of the capacitor 118d may be smaller or larger than that depicted in FIG. 3B. For example, in an embodiment, the electric field 128 of the capacitor 118d may encompass an entirety of the cross-sectional area of the syringe barrel zone 124 proximate to the capacitor 118d.

Disturbances in the electric field 128 (e.g., a reduction of the strength of the electric field or a complete blockage of the electric field) may cause changes to the sensed capacitance between the plates 126a, 126b. For example, when the syringe 116 is filled with air in the region of the syringe barrel zone 124 that is coincident with the electric field 128, the capacitance between the plates 126a, 126b may be at a first value. Likewise, when the syringe 116 is filled with a fluid (e.g., contrast media) in the region of the syringe barrel zone 124 that is coincident with the electric field 128, the capacitance between the plates 126a, 126b may be at second value. The different values may be due to a difference between the dielectric properties of air and the dielectric properties of the fluid. Furthermore, different types of fluids may have different dielectric properties. By determining whether the capacitance of the capacitor 118d is at the first level or the second level, and taking into account the dielectric properties of the fluid being sensed, a determination as to whether air or fluid is present in the region of the syringe barrel zone 124 that is coincident with the electric field 128 may be made. In another method of determining whether fluid or air is present, a threshold value between the first level and the second level may be generated and a determination as to whether air or fluid is present in the region of the syringe barrel zone 124 may be made based on whether the measured capacitance is above or below the threshold value.

It may be possible for a vacuum to be formed within the syringe barrel zone 124. For example, this may occur as a result of retracting the plunger body 92 at a rate greater than the flow rate of the fluid into the syringe barrel zone 124, thus resulting in cavitation. In such instances, the vacuum may be detected with the same apparatuses and methods as described herein with regard to the detection of air. Accordingly, where the detection of air is discussed herein, such discussions may also apply to the detection of a vacuum.

The determination of whether fluid or air is present may be performed by fluid level determination logic 39 (FIG. 1). The fluid level determination logic 39 may be operable to interpret signals from the capacitors 118a-118h and/or other sources (e.g., an angle detector for the powerhead 50, an RFID tag on the syringe 116 identifying the type of fluid within the syringe) and estimate the volume of fluid within the syringe 116 and/or detect air within the syringe 116. The estimation of volume of fluid within the syringe may also be based on previously-known syringe parameters (e.g., inner diameter, barrel length, total volume). Such previously-known syringe parameters, along with the signals from the capacitors 118a-118h and/or other sources, may be used to calculate the estimated volume of fluid within the syringe 116. The estimated volume of fluid may be displayed by any appropriate display (e.g., display 44, GUI 52). The fluid level determination logic 39 may be disposed in any appropriate location or combination of appropriate locations. For example, as shown in FIG. 1, the fluid level determination logic 39 may be disposed within the powerhead 12. In another example, the fluid level determination logic 39 may be disposed within the sensor electronics 132.

As illustrated with respect to capacitor 118d in FIG. 3B, each of the capacitors 118a-118h of the capacitive fluid detector 112 may be in the form of two substantially coplanar plates arranged side by side. Other appropriate capacitor plate configurations may be utilized. For example, the capacitor plates may be non-coplanar, such as where they are angled relative to each other and are facing the center of a syringe. The relative positions of the capacitor plates of each of the capacitors 118a-118h may be such that a vector extending perpendicularly from one of the capacitor plates does not intersect the other.

Continuing using capacitor 118d for exemplary purposes, the output of the capacitive fluid detector 112 with respect to capacitor 118d may be digital, in that below a predetermined sensed capacitance, the output of the capacitive fluid detector 112 with respect to capacitor 118*d* may be at a first level (e.g., zero volts), and above a predetermined sensed capacitance, the output of the capacitive fluid detector 112 with respect to capacitor 118*d* may be at a second level (e.g., five volts). In this regard, the first level output may correspond to a condition where air is within the syringe barrel zone 124 where it intersects with the electric field 128 of capacitor 118*d*, and the second level output may correspond to a condition where fluid is within the syringe barrel zone 124 where it intersects with the electric field 128. Accordingly, the output of the capacitive fluid detector 112 may be used to indicate the presence or absence of fluid within the syringe barrel zone 124 where it intersects with the electric field 128. Similarly, the other capacitors 118*a*-118*c*, 118*e*-118*h*, may be similarly used to determine the presence or absence of fluid within the syringe barrel zone 124 where the syringe barrel zone 124 intersects with the electric fields of the other capacitors 118*a*-118*c*, 118*e*-118*h*.

In the arrangement illustrated in FIG. 3A, capacitors 118*a*-118*h* are arranged along the longitudinal axis 120 of the syringe barrel zone 124. The first capacitor 118*a* may be disposed at a first end the syringe barrel zone 124. The last capacitor 118*h* may be disposed at a nozzle 122 end of the syringe 116 opposite from the first end of the syringe barrel zone 124. The remaining six capacitors 118*b* through 118*g* may be disposed at regular intervals between the two end capacitors 118*a*, 118*h*. Thus the capacitors 118*a*-118*g* may each be separated by a distance equal to about 14% of the total length of the syringe barrel zone 124. Accordingly, the capacitive fluid detector 112, with individual capacitors 118*a*-118*h* operating in a digital mode, may be operable to determine the level of fluid within the syringe barrel zone 124 to within 14% of the actual level of fluid within the syringe barrel zone 124. For example, when fluid is sensed at capacitors 118*a* through 118*f* and no fluid is sensed at capacitors 118*g* and 118*h*, it can be inferred that the syringe barrel zone 124 is at least 71% full since capacitors 118*a* through 118*f* sense fluid. Furthermore, it can be inferred that the syringe barrel zone 124 is at most 85% full since capacitors 118*g* and 118*h* sense no fluid. Thus, it may be inferred that the volume of fluid within the syringe is between 71% and 85% of the syringe barrel zone 124. Such a situation, where no fluid is sensed at capacitors (e.g., capacitors 118*g*-118*h*) toward the nozzle 122 end of the syringe 116 while the remaining capacitors (e.g., capacitors 118*a*-118*f*) sense fluid, may be indicative of an air pocket disposed in the nozzle 122 end of the syringe 116. It will be appreciated that when all capacitors 118*a*-118*h* sense fluid, it may be inferred that the syringe 116 is substantially 100% full, and when none of the capacitors 118*a*-118*h* sense fluid, it may be inferred that the syringe 116 is substantially empty or not installed on the syringe housing 110.

The capacitive fluid detector 112 may be used to confirm and/or determine the volume of fluid within the syringe 116 upon initial installation of the syringe 116 onto the syringe housing 110. For example, where the syringe barrel zone 124 is 125 ml, and possible syringe 116 initial fill volumes (e.g., the amount of fluid in the syringe 116 at the time of installation onto the syringe housing 110) are 125 ml, 100 ml, 50 ml, and 0 ml, the capacitive fluid detector 112 may be operable to distinguish which initial fill volume syringe 116 has been installed onto the syringe housing 110.

Furthermore, in certain embodiments, the individual capacitors 118*a*-118*h* may be distributed along the length of the syringe barrel zone 124 in a non-uniform manner. Non-uniform distribution may allow for the individual capacitors 118*a*-118*h* to be positioned such that they may be used to distinguish between various known initial fill volumes. For example, and using the preceding example, uniformly distributed individual capacitors 118*a*-118*h* may not be able to distinguish a syringe 116 that is 75% full from a syringe 116 that is 80% full. However, by strategically placing a capacitor of the individual capacitors 118*a*-118*h* in the region of the syringe corresponding to, for example, 78% full, that capacitor could be used to distinguish between a 75% full syringe (where that capacitor would not sense any fluid) and an 80% full syringe (where that capacitor would sense fluid).

Since the powerhead 50 may determine the position of the plunger body 92 through other means (e.g., an encoder interconnected to the drive screw 66), the above capacitive sensing may be used to confirm that the expected volume of fluid within the syringe 116 is present. In instances where the sensed volume of fluid does not agree with the expected volume, the system may generate an alarm and/or cease any current injection process. Such disagreement may be an indication of air or vacuum unexpectedly present within the syringe barrel zone 124 and/or the installation of a syringe 116 with the incorrect initial volume of fluid (e.g., where syringe 116' has been installed but where syringe 116 was expected).

The capacitive fluid detector 112 may include any appropriate number of capacitors, including more or fewer capacitors than the eight capacitors 118*a*-118*h* illustrated in FIG. 3A. The quantity and distribution of capacitors may be dependent on the desired function of the capacitive fluid detector 112. For example, where it is desired that the capacitive fluid detector 112 be operable to distinguish between the syringe 116 and the syringe 116', the capacitive fluid detector 112 may only include two capacitors, such as capacitor 118*b* and capacitor 118*g*. In such a configuration, capacitor 118*g* may be used to detect the presence of either syringe 116 or syringe 116' since both syringes 116, 116' would position fluid within the electric field of capacitor 118*g* upon initial installation. Capacitor 118*b* could then be used to detect which type of syringe (syringe 116 or syringe 116') has been installed, since if syringe 116 has been installed, fluid would be positioned within the electric field of capacitor 118*b*, whereas if syringe 116' has been installed, no fluid would be positioned within the electric field of capacitor 118*b*. Accordingly, a unique feature of embodiments described herein may be that an electric field produced by the capacitive fluid detector 112 may intersect with the syringe barrel zone 124 at a plurality of discrete locations (e.g., proximate to capacitor 118*b* and capacitor 118*g*) separated by a discrete distance along the longitudinal axis 120 (e.g. such as the distance between capacitor 118*b* and capacitor 118*g*, which is greater than half the length of the syringe barrel zone 124).

The output of the capacitive fluid detector 112 with respect to the capacitors 118*a*-118*h* may be analog. For example, with respect to capacitor 118*d*, the sensed capacitance may be related to the volume of fluid within the electric field 128 of the capacitor 118*d*. For instance, the sensed capacitance may decrease as the level of the fluid within the electric field 128 increases since the fluid may have a lower dielectric constant than air. Accordingly, when the level of fluid within the syringe barrel zone 124 is such that fluid occupies a portion of the electric field 128, a more precise determination (as compared to when the capacitors 118*a*-118*h* are used in a digital mode) of the total volume of fluid within the syringe barrel zone 124 may be made. Furthermore, the electric field of the capacitor 118*d* may have a length along the longitudinal axis 120 that corresponds to the length of the capacitor 118*d* along the longitudinal axis 120. As such, when the level of fluid within the syringe barrel zone 124 is such that fluid occupies a portion (e.g., less than all) of the electric field 128, the capacitance of capacitor 118*d* may be used to estimate the total volume of fluid within the syringe barrel zone 124. In such a situation, the system may verify that the other capacitors 118*a*-118*c* and 118*e*-118*h* have capacitance values that agree with the volume estimation using the capacitance value from capacitor 118*d*. For example, capacitors 118*e*-118*h* may indicate no fluid while capacitors 118*a*-118*c* indicate the presence of fluid, thus indicating that the syringe barrel zone 124 is filled between the region proximate to capacitor 118*d* and the end of the syringe 116 opposite from the nozzle 122.

Figure 4A:
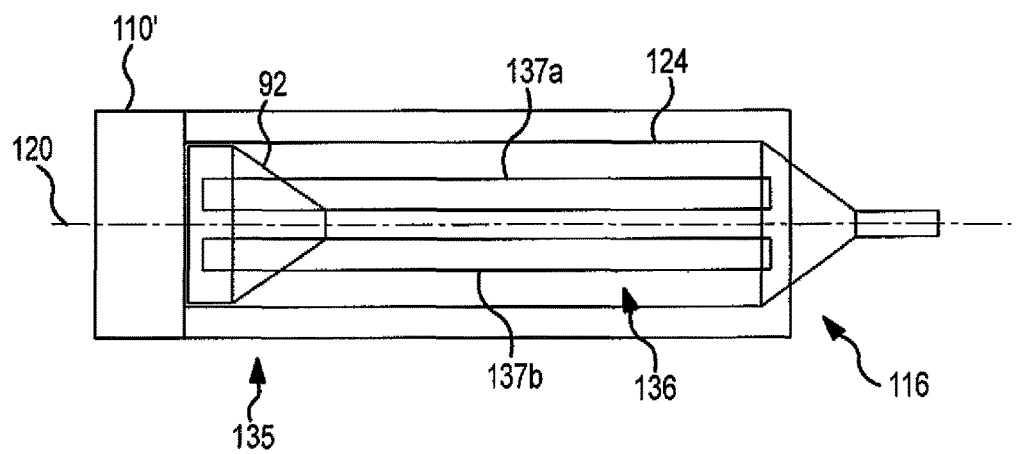
FIG. 4A is a schematic (top view) of a syringe mounted to a syringe housing that includes a capacitive fluid detector.
Figure 4B:
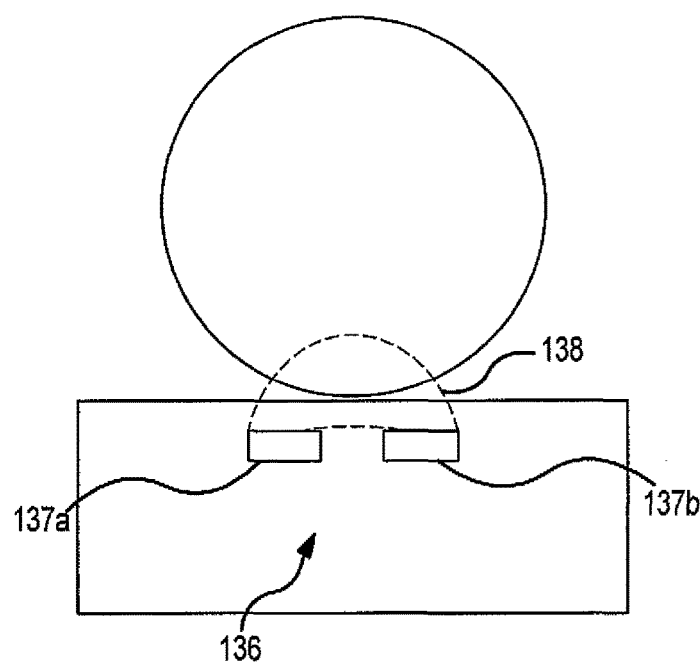
FIG. 4B is a cross-sectional schematic (end view) of the syringe housing and syringe of FIG. 4A.

FIG. 4A is a schematic of a syringe 116 mounted to a syringe housing 110' that includes a capacitive fluid detector 135. FIG. 4B is a cross-sectional schematic view of the syringe 116 and syringe housing 110' of FIG. 4A. The capacitive fluid detector 135 includes a single capacitor 136 whose length along the longitudinal axis 120 of the syringe 116 corresponds to the length of the syringe barrel zone 124. Similar to the analog configuration described above with reference to FIG. 3A, the capacitance of the capacitor 136 may vary as the volume of fluid within the syringe barrel zone 124 varies. Accordingly, the level of fluid within the syringe barrel initial fluid line 124 may be inferred from a measured capacitance value for the capacitor 136.

As illustrated with respect to capacitor 136 in FIG. 4B, the capacitor 136 may be in the form of two substantially coplanar plates 137*a*, 137*b* arranged side by side. Other appropriate capacitor plate configurations may be utilized. For example, the capacitor plates may be non-coplanar, such as where they are angled relative to each other and are facing the center of the syringe. The relative positions of the capacitor plates 137*a*, 137*b* of the capacitor 136 may be such that a vector extending perpendicularly from one of the capacitor plates does not intersect the other.

The length of the capacitor 136 along the longitudinal axis 120 may be less than, equal to, or greater than the length of the syringe barrel zone 124. For example, the length of the capacitor 136 may be selected such that an electric field 138 of the capacitor 136 penetrates the syringe barrel zone 124 along the entire length of the syringe barrel zone 124. In another example, the length of the capacitor 136 may be selected such that an electric field 138 of the capacitor 136 penetrates the syringe barrel zone 124 along a portion of the syringe barrel zone 124 equal to at least half the total length of the syringe barrel zone 124. In such a configuration, the capacitor 136 may correspond to a portion of the syringe barrel zone 124 such that the capacitor 136 may be used to distinguish between different initial fluid volumes. In another configuration, the length of the capacitor 136 may correspond to the entire length of the syringe barrel zone 124 so that the capacitor 136 may be used to determine the volume of fluid within the syringe barrel zone 124 for any amount between empty (no fluid present) and full.

Figure 5A:
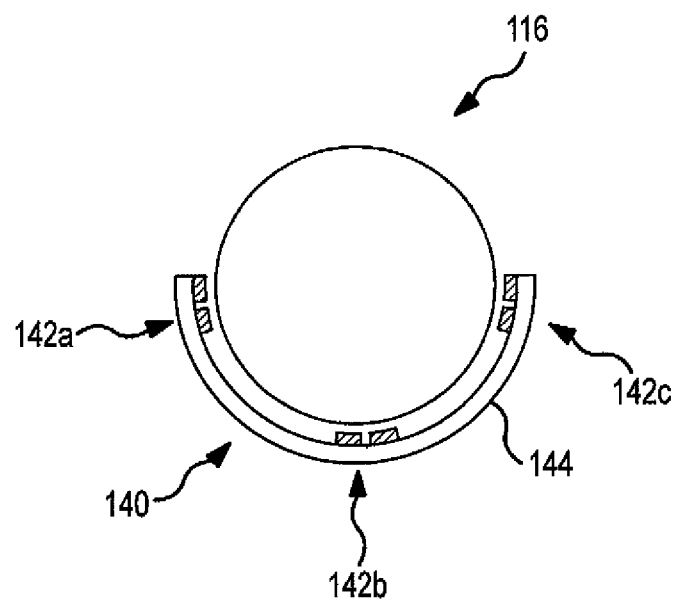
FIGS. 5A and 5B are cross-sectional schematics (end views) of alternate embodiments of a syringe and syringe housing that includes a capacitive fluid detector.

FIG. 5A is a cross sectional schematic view of alternate embodiment wherein syringe 116 is mounted to a syringe housing (not shown) that includes a capacitive fluid detector 140 that includes redundant capacitors 142*a*-142*c*. The capacitors 142*a*-142*c* may each be configured similarly to the capacitor 136 of FIG. 4A. Alternatively, the capacitors 142*a*-142*c* may be a series of discrete capacitors similar to the capacitors 118*a*-118*h* of FIGS. 3A through 3C. The capacitors 142*a*-142*c* may be arranged such that they each coincide with the same portion along the length of the syringe 116. In this regard, each of the capacitors 142*a*-142*c* may be operable to generate an electric field that is capable of detecting fluid within the syringe 116. Accordingly, when the powerhead 50 is oriented with the syringe 116 pointing straight up or straight down, each of the capacitors 142*a*-142*c* may be disposed to independently measure the same fluid level within the syringe 116.

Such independent measurements can be used to filter out certain anomalies. In this regard, the power injector 40 may be operable to compare the determined capacitance of the three capacitors 142*a*-142*c* and filter out anomalous readings. For example, if an external object, such as an operators hand or an electronic device, causes capacitor 142*b* to have an erroneous reading, while the other two capacitors 142*a*, 142*c* are not affected by the external object, the power injector 40 may be operable to ignore the erroneous reading of capacitor 142*b*. The power injector 40 may compare the readings from each of the capacitors 142*a*-142*c* and determine that two of the capacitors 142*a*, 142*c* have a capacitance that indicates a certain level of fluid, while capacitor 142*b* indicates a different level of fluid (due to the presence of the external object). In such a situation, the power injector 40 may disregard the reading of capacitor 142*b* and consider the volume of fluid to be indicated by the capacitance of the two agreeing capacitors 142*a*, 142*c*. Such a situation is illustrated graphically in FIG. 6.

Figure 6:
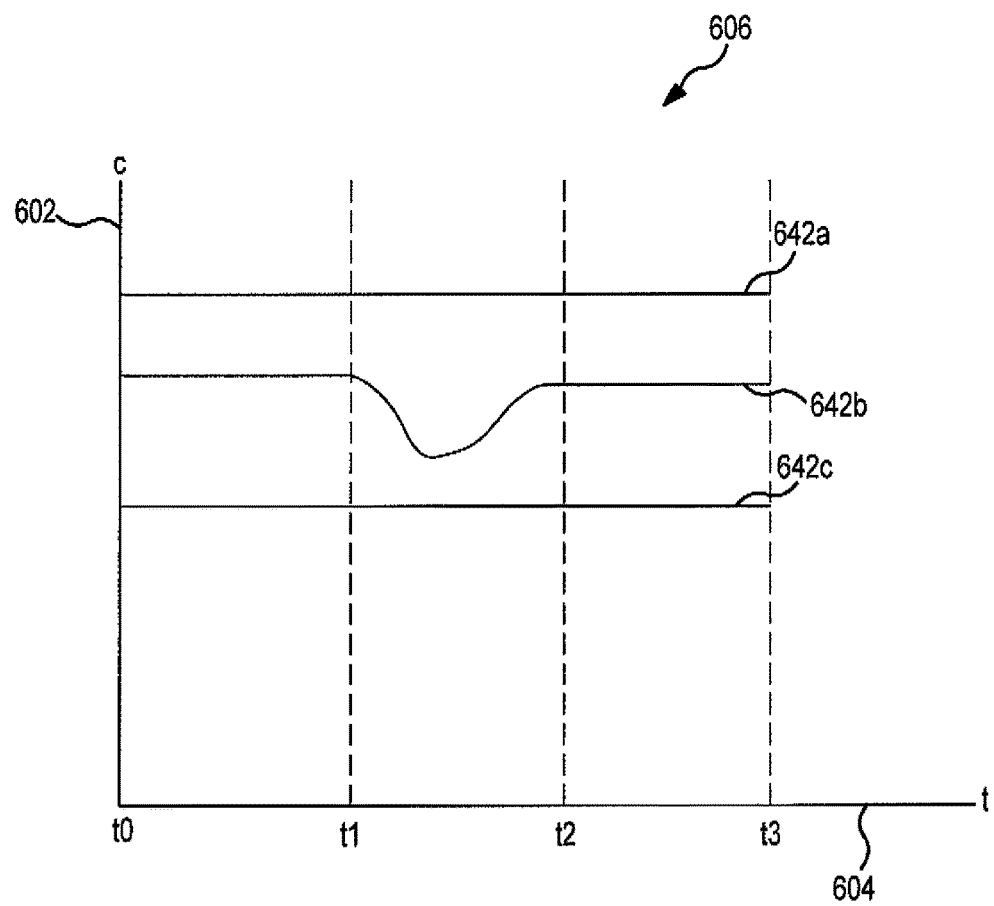
FIG. 6 is a graph illustrating a noise event on a capacitor of a capacitive fluid detector.

Graph 600 of FIG. 6 displays measured capacitance (C) on the vertical axis 602 and time (t) on the horizontal axis 604. Graph 600 depicts operation during a steady state (e.g., no plunger movement) period from t0 to t3. During the period from t0 to t3, a signal 642*a* from capacitor 142*a* and a signal 642*c* from capacitor 142*c* are constant while a signal 642*b* from capacitor 142*b* shows a decrease in value during the time between t1 to t2. Since no corresponding reduction in value is present in the signals 642*a* and 642*c* from capacitors 142*a* and 142*c*, respectively, the power injector 40 (or any appropriate part of the power injector 40) may assume that the signal 642*b* from capacitor 142*b* during the time between t1 to t2 is erroneous and ignore or discount the signal 642*b* during the time between t1 to t2. For the time between t1 to t2, the power injector 40 may preferentially (e.g., exclusively) rely on the signals 642*a*, 642*c* from capacitors 142*a* and 142*c* to estimate fluid volume within the syringe 116. It will be appreciated that the signals 642*a*-642*c* during, for example, the time between t0 to t1 may each represent the same value for volume of fluid within the syringe 116 despite their differing capacitance values. The values may be different due to capacitor configuration and/or their position relative to the volume of fluid being measured. In another configuration, the capacitors 142*a*-142*c* may be selected, arranged, and/or calibrated such that they produce similar readings to each other for any given volume of fluid present within the syringe 116. Other appropriate filtering methods known to those skilled in the art used to determine a reading when redundant sensors are used may be incorporated into the power injector 40.

Figure 7:
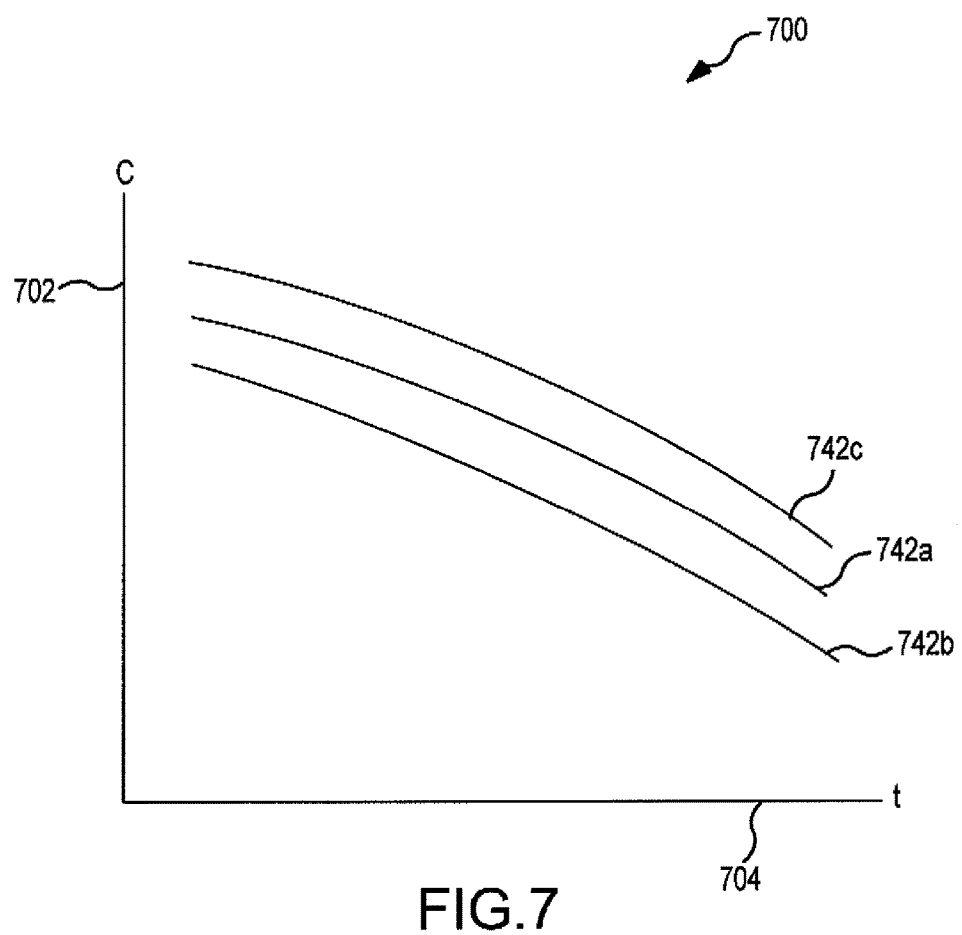
FIG. 7 is a graph illustrating measured capacitance vs. time during a time period where the volume of fluid within a syringe is changing.

As in Graph 600, Graph 700 of FIG. 7 displays measured capacitance (C) on the vertical axis 702 and time (t) on the horizontal axis 704. Graph 700 illustrates a condition where the volume of fluid within the syringe 116 is changing and signals 742*a*, 742*b*, and 742*c* from capacitors 142*a*, 142*b*, and 142*c*, respectively, each track the change in volume. As no single signal is changing at a different rate than the other signals, the power injector 40 may, for any given time, interpret each signal (or a combination signals) to accurately represent the volume of fluid within the syringe 116. As in Graph 600, the values of the signals 742*a*-742*c* may be different due to capacitor configuration and/or their position relative to the volume of fluid being measured.

Referring to FIG. 5A, the capacitors 142a-142c may be mounted along a support 144 that may be shaped to follow the contour of the syringe 116. Such a configuration may be advantageous since the individual capacitors 142a-142c may be disposed in close proximity to the syringe 116. The support 144 and the individual capacitors 142a-142c may be constructed using flexible PCB manufacturing techniques and/or by mounting the plates of the capacitors 142a-142c onto the curved support 144. Any other appropriate method of construction that may be used to create the curved support 144 and capacitors 142a-142c of FIG. 5A may be incorporated.

Figure 5B:
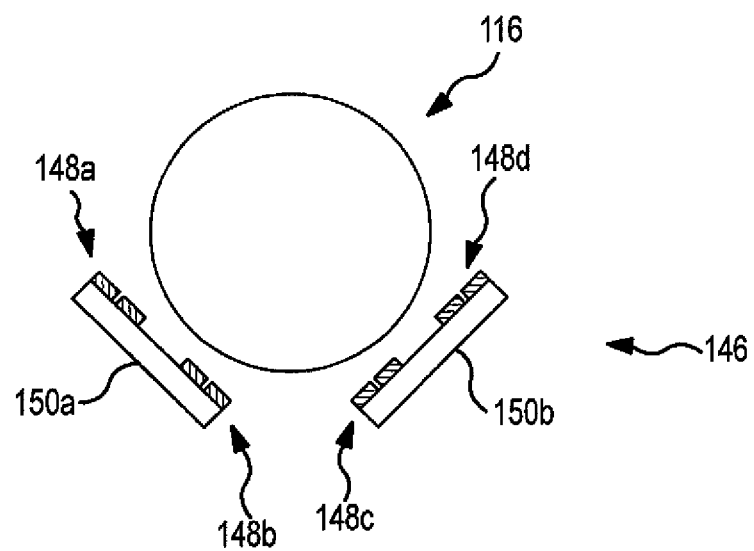

FIG. 5B illustrates an alternate configuration where a capacitive fluid detector 146 comprises individual capacitors 148a-148d arranged on generally flat supports 150a, 150b. Due to the flat configuration of the supports 150a, 150b, and the individual capacitors 148a-148d disposed thereon, the capacitive fluid detector 146 may be manufactured using standard PCB manufacturing techniques or any other appropriate technique.

Both the capacitive fluid detector 140 and the capacitive fluid detector 146 may be disposed within (e.g., encapsulated) a corresponding syringe housing (not shown), similar to the capacitive fluid detector 112 within the syringe housing 110 described with reference to FIGS. 3A-3C. Any appropriate number of redundant capacitors may be used.

Methods of operating injection systems that include syringe housings with capacitive fluid detectors such as those described above with reference to FIGS. 3A through 5B will now be described. A first step in such a method may be to install the syringe 116 onto an injection device of the injection system. The injection system may, for example, be the power injector 40 described. The injection device may, for example, be the powerhead 50 described above. Installing the syringe 116 onto the injection device may include placing the syringe 116 onto a syringe housing (e.g., syringe housing 110 or syringe housing 110') such that the syringe 116 is proximate to a capacitive fluid detector (e.g., capacitive fluid detector 112, capacitive fluid detector 135, capacitive fluid detector 140, or capacitive fluid detector 146) within the syringe housing. Installing the syringe 116 onto the syringe housing may include coupling a ram 74 of the injection device to a plunger body 92 of the syringe 116. In this regard, the ram 74 of the injection device may be operable to extend and/or retract the plunger body 92 of the syringe 116.

The installation of the syringe 116 onto the injection device may include identifying the volume and/or type of fluid within the syringe 116. This identification step may be separate from sensing fluid within the syringe 116 with the capacitive fluid detector. This identification step may include communicating the volume and/or type of fluid within the syringe 116 to the power injector 40 (or component thereof) using any appropriate means. For example, an operator may manually enter the volume and/or type of fluid within the syringe 116 into the user interface 11 of the power injector 40. For further example, the power injector 40 may be operable to read an attribute of the syringe 116 to determine the volume and/or type of fluid within the syringe 116. The attribute may be a visual indicator, such as the barcode or other label, and/or the attribute may be in the form of an RFID tag associated with the syringe 116.

The installation of the syringe 116 onto the injection device may be followed by capacitively sensing the presence of fluid within the installed syringe 116. The capacitively sensing may be performed while the powerhead 50 is pointing upward or downward. In such an orientation (e.g., upward or downward pointing), any fluid within the syringe 116 may be distributed such that any cross-sectional plane perpendicular to the longitudinal axis may be uniform (e.g., all fluid or all air). Such orientation may simplify the detection of air within the syringe 116. Additionally, the capacitively sensing may be performed while the powerhead 50 is at an angle (e.g. relative to upward or downward pointing) with the injection system taking into account that, if there is air within the syringe 116 between the plunger body 92 and the nozzle 122, the interface between fluid and air within the syringe 116 may be at an angle corresponding to the angle of the powerhead 50.

In the case of a capacitive fluid detector that includes a plurality of discrete capacitors, such as the capacitive fluid detector 112 of the FIG. 3A, the capacitively sensing may include sensing the presence of fluid within the installed syringe 116 with a first portion of the plurality of capacitive sensors 118a-118h, and sensing no fluid within the installed syringe 116 with a second portion of the plurality of capacitor sensors 118a-118h. Such capacitive sensing may be performed prior to injecting any of the fluid from within the syringe 116 into a patient. The capacitively sensing of fluid may be followed by estimating a total volume of fluid within the syringe 116 based on the capacitive sensing. Such an estimation may, for example, include dividing the number of capacitive sensors that sensed the presence of fluid by the total number of capacitive sensors of the capacitive fluid detector 112 to arrive at an estimation of the percentage fill of the syringe 116. Moreover, such an estimation may, for example, include looking up, in a lookup table, the total volume of fluid within the syringe 116 that corresponds to the number of capacitive sensors that sensed the presence of fluid.

In the case of a capacitive fluid detector that includes a single elongated capacitor, such as the capacitive fluid detector 135 of FIGS. 4A and 4B, the capacitively sensing may include detecting a capacitance value between the individual plates of the capacitor 136. The detected capacitance value may then be used by the injection system to estimate the volume of fluid within the syringe 116. This estimation may be through a calculation and/or through looking up the capacitance value in a lookup table.

After the total volume of fluid within the syringe 116 is estimated based on the capacitive sensing, the injection system may verify that the estimated total volume of fluid within the syringe 116 corresponds to the fluid volume determined in the identifying step (e.g., manually entered, automatically entered).

The estimation of the total volume of fluid based on the capacitive sensing may also factor in that there may be a limited number of different initial syringe fluid volumes. For example, there may be only a limited number of discrete initial volumes of fluid in the syringe 116 that are operable to be installed onto the syringe housing 110. For instance, syringes operable to be installed onto the syringe housing 110 may only be provided in 125 ml, 100 ml, 50 ml and 0 ml (e.g., empty) initial fill volume sizes. In such an operating environment, the capacitive fluid detector 112 may only be required to initially distinguish between the aforementioned differing initial volumes.

Another step in a method of operating and injection system that includes a capacitive fluid detector may be to move the ram 74 of the powerhead 50 to move the plunger body 92 of the syringe 116. While the plunger body 92 is moving, the capacitive fluid detector may capacitively sense fluid within the syringe barrel zone 124 a plurality of times. Furthermore, the injection system may estimate a volume of fluid within the syringe 116 at each of the plurality of times where fluid within the syringe barrel zone 124 was capacitively sensed. In this regard, the level of fluid within the syringe 116 may be known while the plunger body 92 is moving. The capacitively sensing and total volume estimating may be performed continuously while the plunger body 92 is moving. The moving of the plunger body 92 may be a retraction of the plunger body 92 (e.g., to draw fluid into the syringe barrel zone 124), or it may be an extension of the plunger body 92 (e.g., to eject fluid from the syringe barrel zone 124).

By capacitively sensing fluid levels as the plunger body 92 is being retracted, the injection system may be operable to confirm that the retraction of the plunger body 92 is drawing fluid into the syringe barrel zone 124. For example, the injection system may know the position of the plunger body 92 (e.g., through an encoder interconnected to the drive screw 66) and therefore be able to calculate an expected volume of fluid within the syringe barrel zone 124 associated with the position of the plunger body 92. If the volume of fluid determined by the capacitively sensing of fluid within the syringe barrel zone 124 does not agree with the expected volume based on the plunger body 92 position, the injection system may sound an alarm and/or stop moving the plunger body 92. Such a condition may be an indication that air has entered into the syringe barrel zone 124 in the volume between the plunger body 92 and the nozzle 122 of the syringe 116. This may be due to a leak in the injection system and/or an empty fluid source.

In any of the above steps where fluid is capacitively sensed, the capacitively sensing may further include sensing fluid within the syringe barrel zone 124 with first, second and third capacitive sensors arranged in a redundant configuration. In this regard, the method may further include identifying erroneous readings based at least partly on comparing the outputs from the first, second and third capacitive sensors.

The fluid level determination logic 39 may be implemented in any appropriate manner, including without limitation in any appropriate software, firmware, or hardware, using one or more platforms, using one or more processors, using memory of any appropriate type, using any single computer of any appropriate type or a multiple computers of any appropriate type and interconnected in any appropriate manner, or any combination thereof. The fluid level determination logic 39 may be implemented at any single location or at multiple locations that are interconnected in any appropriate manner (e.g., via any type of network).

Figure 8:
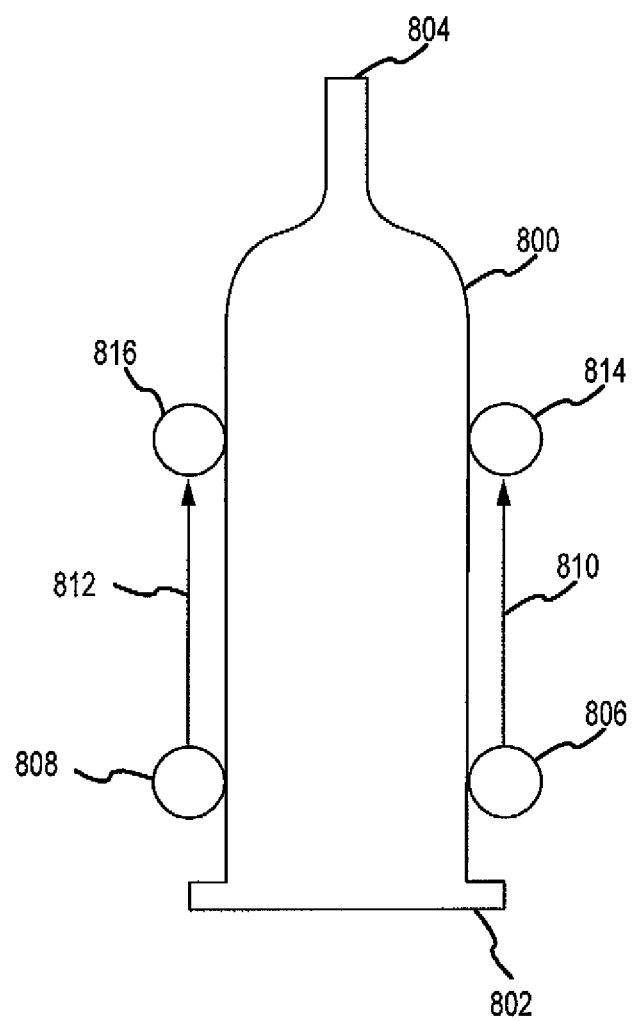
FIG. 8 is a schematic depicting a user sliding two fingers along the barrel of a syringe.

Capacitive signal changes caused by human interaction proximate to the syringe barrel zone 124 may be used to provide inputs into the power injector 40. One example of a type of human interaction that may serve as an input to the power injector 40 is illustrated in FIG. 8 which schematically shows a syringe 800 positioned on the power injector 40 (not shown in FIG. 8). A user may wish to instruct the power injector 40 to perform a purge operation which would entail moving the ram 20 (not shown in FIG. 8) forward to purge the syringe 800 of any fluid therein. To instruct the power injector 40 to perform the purge, the user may place his or her thumb and forefinger from one hand on each side of the syringe 800 near the end 802 of the syringe 800 opposite from a nozzle 804. This finger position is illustrated by circles 806 and 808 adjacent to the syringe 800. The user may then sweep the thumb and forefinger along the syringe toward the nozzle 804 as illustrated by arrows 810 and 812 to a finger position illustrated by circles 814 and 816. This motion simulates the action of the ram 20 during the purge operation and thus may be intuitive and easily remembered by a user.

Figure 9:
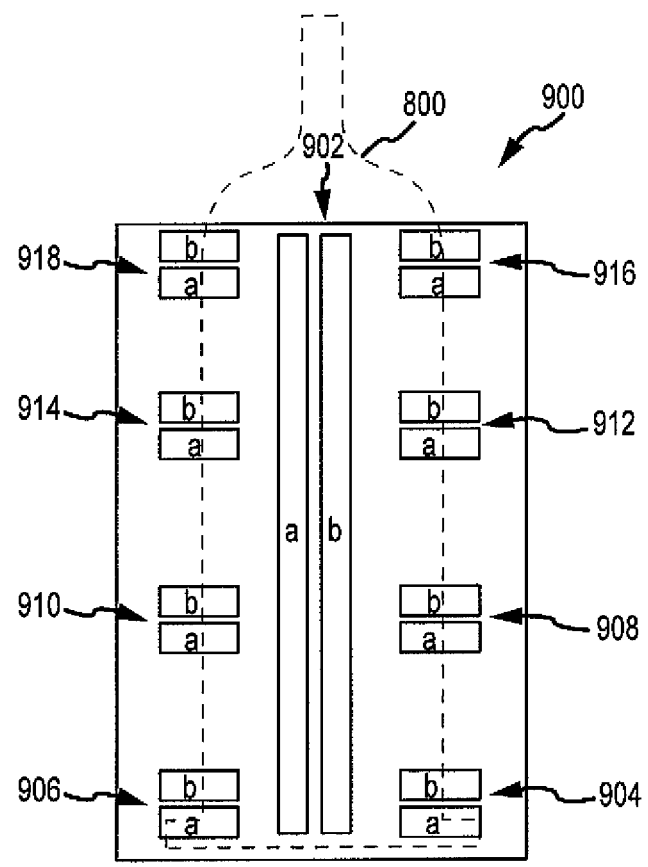
FIG. 9 is a schematic of a capacitive user input detector.

FIG. 9 illustrates a capacitive user input detector in the form of an exemplary arrangement of capacitors 900 that may be used to detect the user input illustrated in FIG. 8. The arrangement 900 includes a central capacitor 902 arranged parallel to the orientation of how the syringe 800 (shown in phantom in FIG. 9) may be mounted to the power injector 40. The central capacitor 902 may include two substantially coplanar plates 902*a*, 902*b* arranged side by side in a manner similar to substantially coplanar plates 137*a*, 137*b* of FIG. 4B. The arrangement of capacitors 900 further includes a plurality of peripheral capacitors (capacitors 904, 906, 908, 910, 912, 914, 916 and 918) disposed on each side of the central capacitor 902. The peripheral capacitors may be arranged to detect finger placement and/or finger motion of a user when the user's fingers (as used herein, a thumb is considered a finger) are placed and/or moved along a side of the syringe 800. Each of the peripheral capacitors may include a pair of substantially coplanar plates (each labeled a orb in FIG. 9) arranged side by side. The peripheral capacitors may be arranged and configured such that the power injector 40 is operable to distinguish along which side of the syringe 800 a finger is placed. Thus, a finger placed along the right side (as oriented in FIGS. 8 and 9) of the syringe 800 proximate to peripheral capacitor 904 may be detected as being along the right side of the syringe 800 while a finger placed along the left side of the syringe 800 proximate to peripheral capacitor 906 may be detected as being along the left side of the syringe 800. In variations of the configuration of FIG. 9, more or fewer peripheral capacitors may be used. Additionally, each capacitor may be positioned in any appropriate location. Moreover, variations of the arrangement 900 may not include the central capacitor 902.

Turning back to the example of the arrangement of capacitors 900 of FIG. 9, the position of a user's finger along a side of the syringe 800 may be detected in a manner similar to as discussed above with relation to the detection of fluid level. In this regard, the capacitance between plates a and b of peripheral capacitor 904 may be at a first value when a user's finger is in the region of the electric field of peripheral capacitor 904 and at a second value when the user's finger is not present. The different values may be due to a difference between the dielectric properties of air and the user's finger. As the user sweeps a finger along the right side of the syringe 800 from proximate to peripheral capacitor 904 toward peripheral capacitor 908, the sensed electric fields of both peripheral capacitor 904 and peripheral capacitor 908 may change (e.g., in opposite directions), and these changes may be interpreted as movement of a finger along the right side of the syringe 800. In this manner, the arrangement of capacitor 900 may be used to detect the presence and movement of a user's fingers along the sides of the syringe 800. Thus, the movement of the user's fingers described with reference to FIG. 8 may be detected and used as an input command to the power injector 40 to initiate, for example, a purge operation.

Figure 10:
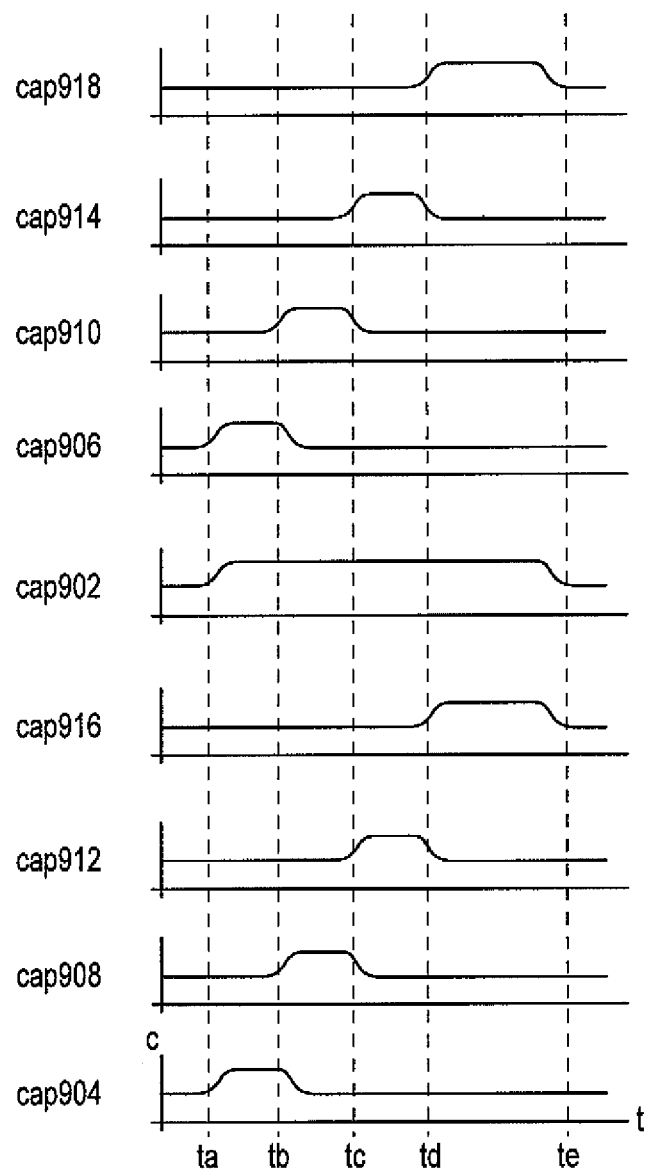
FIG. 10 illustrates a group of signal responses that may occur when a user performs the finger movement shown in FIG. 8.

The power injector 40 may check for specific signal responses to sense a user input. FIG. 10 illustrates a group of signal responses that may occur when a user performs the finger movement shown in FIG. 8 requesting the power injector 40 to perform a purge operation. Each graph of FIG. 10 illustrates a signal that may be detected at each correspondingly numbered capacitor of FIG. 9. Accordingly, at time ta, the user may first place their thumb and forefinger in the positions illustrated by circles 806 and 808 and capacitors 904 and 906 may experience a change in sensed capacitance as shown by the change in capacitance (c) in corresponding Graphs cap904 and cap906 at time ta. Similarly, the capacitance measured by the central capacitor 902 may change when the thumb and forefinger are present, as illustrated in Graph cap902 at ta. As the user slides his or her fingers along the syringe barrel in the direction of arrows 810 and 812 of FIG. 8, the sensed capacitance at the peripheral capacitors may change. For example, at time tb, as the thumb and forefinger move away from capacitors 904 and 906 and move toward capacitors 908 and 910, the sensed capacitance will change for both sets of capacitors as illustrated in Graphs cap904, cap908, cap906 and cap910. Similar changes may occur at tc and td. This pattern will continue progressively through to cap916 and cap918 as the user moves his or her thumb and forefinger to the positions illustrated by circles 814 and 816. Moreover, the user may dwell at the positions illustrated by circles 814 and 816, and as such, the sensed capacitance at capacitor 916 and capacitor 918 may occur for a relatively longer time period than the other peripheral capacitors. This is illustrated by Graphs cap916 and cap918 which show an extended duration of signal relative to the other graphs for peripheral capacitors between times td and te. As illustrated, the capacitance change measured by the central capacitor 902 may last for the entire duration that the user's fingers are positioned along the syringe 800.

To minimize inadvertent purges, the power injector 40 may require appropriate signal responses on the appropriate capacitors at the appropriate times. For example, if any of the signals shown in FIG. 10 were not present, were present in a different order than as illustrated in FIG. 10, or if the durations of the signals deviated from a predetermined length by a predetermined amount, the power injector 40 may not interpret such signals as an instruction to perform a purge operation. Moreover, other factors may also be used to determine if the power injector 40 should perform a purge operation after receiving the signals as illustrated in FIG. 10. For example, the power injector 40 may include a tilt sensor and the purge function may only be performed when the syringe 800 in the power injector 40 is tilted up. Another example is that the power injector 40 may not perform a purge operation despite receiving the signals as illustrated in FIG. 10 if the power injector 40 is currently performing an injection.

Other inputs performed by human interaction proximate to the syringe barrel zone 124 may be used to provide inputs into the power injector 40. Such functions as syringe fill, increases or decreases to flow rates, emergency stop, syringe removal, and/or RFID data inquiry may be inputted via movement or placement of a user's finger or fingers along the syringe 800. Any other appropriate function may be inputted via such finger movement or placement. Although illustrated as being an input intended to instruct the power injector 40 to perform a purge, the finger motion illustrated in FIG. 8 may be used as an input to instruct the power injector 40 to perform any appropriate operation. For example, instead of the previously described purge operation, the finger motion illustrated in FIG. 8 may be used to instruct the power injector 40 to begin an injection. In another example, the finger motion illustrated in FIG. 8 may be used to input commands where the function to be performed is context sensitive. That is, the same motion may be used to input different context sensitive instructions, such as the finger motion illustrated in FIG. 8 being used to input a purge function when the syringe 800 is pointing up and another different function when the syringe is pointing down.

The arrangement of capacitors 900 may be used to sense user input as discussed above. Additionally, the arrangement of capacitors 900 may be used to perform the fluid level detection functions described herein. Moreover, other capacitor configurations discussed herein with reference to fluid level detection may be used to sense user input in a manner similar to as discussed with reference to the arrangement of capacitors 900. Along these lines, any particular arrangement of capacitors may, where appropriate, be employed to sense fluid levels, sense user inputs, or sense both fluid levels and user inputs.

The interpretation of capacitive signals used for human inputs discussed above may be performed by the same logic as that which determines fluid levels within a syringe (e.g., the fluid level determination logic 39 shown in FIG. 1). Alternatively, the interpretation of capacitive signals used for human inputs may be performed by user input determination logic. Such user input determination logic may be separate from the fluid level determination logic 39 shown in FIG. 1.

The foregoing description of the present invention has been presented for purposes of illustration and description. Furthermore, the description is not intended to limit the invention to the form disclosed herein. Consequently, variations and modifications commensurate with the above teachings, and skill and knowledge of the relevant art, are within the scope of the present invention. The embodiments described hereinabove are further intended to explain best modes known of practicing the invention and to enable others skilled in the art to utilize the invention in such, or other embodiments and with various modifications required by the particular application(s) or use(s) of the present invention. It is intended that the appended claims be construed to include alternative embodiments to the extent permitted by the prior art.

What is claimed:

1. An injection system comprising:
    an injection device comprising a powerhead and a syringe housing, wherein said syringe housing comprises a cradle that extends away from said powerhead;
    a syringe mounted to said injection device, wherein said syringe housing provides an interface between said powerhead and said syringe, wherein said injection device is operable to discharge fluid from said syringe, wherein said syringe comprises a syringe barrel, wherein said syringe barrel has a syringe barrel length along a syringe barrel longitudinal axis, wherein said cradle of said syringe housing extends along said syringe barrel, and wherein said syringe extends above said cradle;
    a capacitive fluid detector disposed along said syringe barrel and enclosed within said cradle of said syringe housing such that said cradle of said syringe housing is disposed between said capacitive fluid detector and said syringe, wherein said capacitive fluid detector comprises a plurality of capacitors, wherein said plurality of capacitors are arranged serially along said syringe barrel length and are spaced from one another along said syringe barrel length, wherein each of said plurality of capacitors is disposed at a different position along said syringe barrel longitudinal axis;
    a syringe barrel zone coextensive with said syringe barrel, wherein said syringe barrel zone comprises a syringe barrel zone length coinciding with said syringe barrel length; wherein said syringe barrel zone comprises a syringe barrel zone longitudinal axis coinciding with said syringe barrel longitudinal axis; and a fluid level determination logic operable to determine a level of a fluid within said syringe barrel zone at least partially based on an output from each capacitor of said plurality of capacitors;

wherein said fluid level determination logic determines whether each said output is either of a first capacitance level or a second capacitance level, with said first capacitance level being associated with a presence of fluid and with said second capacitance level being associated with an absence of fluid; and wherein said fluid level determination logic uses the determination of each said capacitor of said plurality of capacitors either being of said first capacitance level or said second capacitance level to calculate an estimated volume of said fluid in said syringe.

2. The injection system of claim 1, wherein said plurality of capacitors arranged serially along said syringe barrel zone length comprises at least eight individual said capacitors.

3. The injection system of claim 1, wherein each capacitor of said plurality of capacitors comprises a pair of electrodes, wherein each electrode of each pair of electrodes is arranged such that a vector perpendicular to and intersecting said electrode does not intersect any other electrode.

4. The injection system of claim 3, wherein each electrode of said pair of electrodes comprises two substantially coplanar electrodes.

5. The injection system of claim 1, wherein each capacitor of said plurality of capacitors is interconnected to an integrated circuit, wherein for each of said plurality of capacitors, said integrated circuit is operable to produce a bimodal output, wherein a first mode of said bimodal output is in response to a presence of said fluid and a second mode of said bimodal output is in response to a lack of said fluid.

6. The injection system of claim 1, wherein each capacitor of said plurality of capacitors is operable to produce an analog output that varies in response to an amount of fluid within an electric field of said capacitor.

7. The injection system of claim 1, further comprising a user input determination logic operable to determine a user input at least partially based on output from said capacitive fluid detector.

8. The injection system of claim 1, further comprising a capacitive user input detector, wherein an electric field of said capacitive user input detector penetrates said syringe barrel zone within a first region that extends along said syringe barrel zone.

9. The injection system of claim 8, wherein said electric field of said capacitive user input detector penetrates said syringe barrel zone within a second region that extends along said syringe barrel zone, wherein said second region is on an opposite side of said syringe barrel zone than said first region.

10. The injection system of claim 8, further comprising a user input determination logic operable to determine a user input at least partially based on output from said capacitive user input detector.

11. The injection system of claim 1, wherein said injection system is operable to detect a presence of a finger of a user adjacent to said syringe barrel zone.

12. The injection system of claim 1, wherein said injection system is operable to detect a movement of a finger of a user adjacent to said syringe barrel zone.

13. The injection system of claim 1, wherein said syringe housing comprises a faceplate that is installed on the powerhead, and wherein said cradle extends away from said faceplate.

14. The injection system of claim 1, wherein said capacitive fluid detector comprises a printed circuit board (PCB), wherein the plurality of capacitors are disposed on the PCB, and wherein the PCB and plurality of capacitors are sealed within said syringe housing.

* * * * *

UNITED STATES PATENT AND TRADEMARK OFFICE
CERTIFICATE OF CORRECTION

PATENT NO.       : 9,849,237 B2
APPLICATION NO.  : 14/232305
DATED            : December 26, 2017
INVENTOR(S)      : Gibson et al.

It is certified that error appears in the above-identified patent and that said Letters Patent is hereby corrected as shown below:

In the Specification

Column 22, Line 11, delete "operators" and insert therefore --operator's--

Column 26, Line 23, delete "a orb" and insert therefore --a or b--

Signed and Sealed this
Eighth Day of May, 2018

Andrei Iancu
*Director of the United States Patent and Trademark Office*